United States Patent
Masumoto

(10) Patent No.: US 8,893,136 B2
(45) Date of Patent: Nov. 18, 2014

(54) AUTOMATED OPERATION LIST GENERATION DEVICE, METHOD AND PROGRAM

(75) Inventor: Jun Masumoto, Minato-ku (JP)

(73) Assignee: FUJIFILM Corporation, Tokyo (JP)

( * ) Notice: Subject to any disclaimer, the term of this patent is extended or adjusted under 35 U.S.C. 154(b) by 314 days.

(21) Appl. No.: 13/249,537

(22) Filed: Sep. 30, 2011

(65) Prior Publication Data

US 2012/0084783 A1 Apr. 5, 2012

(30) Foreign Application Priority Data

Oct. 1, 2010 (JP) ................................. 2010-223853

(51) Int. Cl.
| | | |
|---|---|---|
| G06F 9/46 | (2006.01) | |
| G06F 9/44 | (2006.01) | |
| A61B 6/03 | (2006.01) | |
| G06T 11/00 | (2006.01) | |
| A61B 6/00 | (2006.01) | |

(52) U.S. Cl.
CPC ................ G06F 9/4443 (2013.01); A61B 6/03 (2013.01); A61B 6/461 (2013.01); G06F 9/4425 (2013.01); G06T 11/00 (2013.01)
USPC .......................................... 718/102; 705/301

(58) Field of Classification Search
USPC ......................................................... 718/102
See application file for complete search history.

(56) References Cited

U.S. PATENT DOCUMENTS

| | | | | |
|---|---|---|---|---|
| 5,005,119 | A * | 4/1991 | Rumbaugh et al. ............ | 718/101 |
| 2003/0103232 | A1* | 6/2003 | Twede .......................... | 358/1.15 |
| 2006/0048094 | A1* | 3/2006 | Kipman et al. ............... | 717/104 |
| 2006/0064321 | A1 | 3/2006 | Sasano | |
| 2006/0067252 | A1* | 3/2006 | John et al. ..................... | 370/261 |
| 2006/0184937 | A1* | 8/2006 | Abels et al. ........................ | 718/1 |
| 2007/0089047 | A1* | 4/2007 | Joshi .......................... | 715/501.1 |
| 2009/0228479 | A1 | 9/2009 | Nishiyama | |
| 2010/0030578 | A1* | 2/2010 | Siddique et al. .................. | 705/3 |
| 2011/0159470 | A1* | 6/2011 | Hradek et al. ................ | 434/262 |

FOREIGN PATENT DOCUMENTS

| | | |
|---|---|---|
| DE | 44 04 649 A1 | 11/1995 |
| EP | 1 475 627 A2 | 11/2004 |
| JP | 2005-161032 A | 6/2005 |
| JP | 2005161032 A | 6/2005 |

OTHER PUBLICATIONS

Fujisawa, Kyoko, Translation of JP 2005161032 A, 2005.*
Extended Search Report dated Jan. 20, 2012, issued in corresponding European patent Application 111182340.8.
European Office Action Application No. 11 183 240.8-1954; Mar. 27, 2013.

* cited by examiner

Primary Examiner — Emerson Puente
Assistant Examiner — Charlie Sun
(74) Attorney, Agent, or Firm — Sughrue Mion, PLLC

(57) ABSTRACT

Selection of operations in a desired order and, as necessary, input of processing parameters by the user are received. Based on each operation corresponding to the received input, operation information, which classifies the operation corresponding to the input into a non-routine operation, which requires input of a processing parameter during execution of an automated operation list, or a routine operation other than the non-routine operation in advance, is obtained. Then, an automated operation list is generated based on the obtained operation information by registering, if the operation corresponding to the input is a routine operation, the operation corresponding to the input in the automated operation list with associating, as necessary, a necessary processing parameter for the operation with the operation, and registering, if the operation corresponding to the input is a non-routine operation, the operation corresponding to the input in the automated operation list.

13 Claims, 10 Drawing Sheets

| OPERATION ID | DESCRIPTION OF OPERATION | CLASSIFICATION | PROCESSING PARAMETER |
|---|---|---|---|
| abcd0001 | CUT OBJECT | NON-ROUTINE | (abcd0001_0001,...) |
| abcd0002 | SELECT OBJECT | NON-ROUTINE | (abcd0002_0001,...) |
| abcd0003 | MEASURE LENGTH | NON-ROUTINE | (abcd0003_0001,...) |
| abcd0004 | FILL MASK | NON-ROUTINE | (abcd0004_0001,...) |
| abcd0005 | SET CPR PATH | NON-ROUTINE | (abcd0005_0001,...) |
| abcd0006 | CORRECT BLOOD VESSEL DIAMETER | NON-ROUTINE | (abcd0006_0001,...) |
| abcd0007 | CHANGE DISPLAY RANGE (CLIP) | ROUTINE | abcd0007_0001,... |
| abcd0008 | GENERATE MOVING IMAGE (SPECIFY RANGE) | ROUTINE | abcd0008_0001,... |
| abcd0009 | ENLARGE/REDUCE MASK | ROUTINE | abcd0009_0001,... |
| abcd0010 | EXTRACT BONE | ROUTINE | abcd0010_0001,... |
| abcd0011 | EXTRACT LIVER | ROUTINE | abcd0011_0001,... |
| abcd0012 | EXTRACT HEART | ROUTINE | abcd0012_0001,... |
| abcd0013 | SEND IMAGE | ROUTINE | abcd0013_0001,... |
| abcd0014 | SELECT DESTINATION OF IMAGE | ROUTINE | abcd0014_0001,... |
| abcd0015 | SELECT WINDOW WIDTH/LEVEL FUNCTION | ROUTINE | abcd0015_0001,... |
| abcd0016 | SET SLIDER VALUE OF WINDOW LEVEL AT XX | ROUTINE | abcd0016_0001,... |
| abcd0017 | SET SLIDER VALUE OF WINDOW WIDTH AT XX | ROUTINE | abcd0017_0001,... |
| abcd0018 | ENLARGE/REDUCE | ROUTINE | abcd0018_0001,... |
| abcd0019 | DISPLAY TOP VIEW OF 3D IMAGE | ROUTINE | abcd0019_0001,... |
| abcd0020 | DISPLAY RIGHT SIDE VIEW OF 3D IMAGE | ROUTINE | abcd0020_0001,... |
| abcd0021 | DISPLAY LEFT SIDE VIEW OF 3D IMAGE | ROUTINE | abcd0021_0001,... |
| abcd0022 | DISPLAY FRONT VIEW OF 3D IMAGE | ROUTINE | abcd0022_0001,... |
| abcd0023 | DISPLAY BOTTOM VIEW OF 3D IMAGE | ROUTINE | abcd0023_0001,... |
| abcd0024 | MASK CHANGING FUNCTION | ROUTINE | abcd0024_0001,... |
| abcd0025 | SELECT COLOR TEMPLATE 1 | ROUTINE | abcd0025_0001,... |
| ... | ... | ... | ... |

| ORDER | DESCRIPTION OF OPERATION | CLASSIFICATION | OPERATION ID | PROCESSING PARAMETER |
|---|---|---|---|---|
| 1 | SELECT 3D IMAGE | ROUTINE | abcdxxxx | abcdxxxx_yyyy,... |
| 2 | SELECT MIP AS DISPLAY METHOD | ROUTINE | abcdxxxx | abcdxxxx_yyyy,... |
| 3 | SELECT WINDOW WIDTH/LEVEL FUNCTION | ROUTINE | abcdxxxx | abcdxxxx_yyyy,... |
| 4 | SET SLIDER VALUE OF WINDOW LEVEL AT 1000 | ROUTINE | abcdxxxx | abcdxxxx_yyyy,... |
| 5 | SET SLIDER VALUE OF WINDOW WIDTH AT 500 | ROUTINE | abcdxxxx | abcdxxxx_yyyy,... |
| 6 | DISPLAY TOP VIEW OF 3D IMAGE | ROUTINE | abcdxxxx | abcdxxxx_yyyy,... |
| 7 | SELECT CUTTER FUNCTION | ROUTINE | abcdxxxx | abcdxxxx_yyyy,... |
| 8 | CUT UNNECESSARY AREA VIA MOUSE OPERATION (CUR SKIN SURFACE OF FACE) | NON-ROUTINE | abcdxxxx | (abcdxxxx_yyyy,...) |
| 9 | DISPLAY FRONT VIEW OF 3D IMAGE | ROUTINE | abcdxxxx | abcdxxxx_yyyy,... |
| 10 | EXECUTE SCREEN CAPTURING | ROUTINE | abcdxxxx | abcdxxxx_yyyy,... |
| 11 | DISPLAY RIGHT SIDE VIEW OF 3D IMAGE | ROUTINE | abcdxxxx | abcdxxxx_yyyy,... |
| 12 | EXECUTE SCREEN CAPTURING | ROUTINE | abcdxxxx | abcdxxxx_yyyy,... |
| 13 | SELECT OBJECT SELECTION FUNCTION | ROUTINE | abcdxxxx | abcdxxxx_yyyy,... |
| 14 | SELECT OBJECT (CEREBRAL ARTERY) | NON-ROUTINE | abcdxxxx | (abcdxxxx_yyyy,...) |
| 15 | DISPLAY FRONT VIEW OF 3D IMAGE | ROUTINE | abcdxxxx | abcdxxxx_yyyy,... |
| 16 | EXECUTE SCREEN CAPTURING | ROUTINE | abcdxxxx | abcdxxxx_yyyy,... |
| 17 | DISPLAY RIGHT SIDE VIEW OF 3D IMAGE | ROUTINE | abcdxxxx | abcdxxxx_yyyy,... |
| 18 | EXECUTE SCREEN CAPTURING | ROUTINE | abcdxxxx | abcdxxxx_yyyy,... |
| 19 | DISPLAY CAPTURE BOX | ROUTINE | abcdxxxx | abcdxxxx_yyyy,... |
| 20 | SPECIFY TRANSFER DESTINATION ("IMAGE STORING SERVER A") | ROUTINE | abcdxxxx | abcdxxxx_yyyy,... |
| 21 | EXECUTE TRANSFER | ROUTINE | abcdxxxx | abcdxxxx_yyyy,... |

AUTOMATED OPERATION LIST GENERATION DEVICE, METHOD AND PROGRAM

BACKGROUND OF THE INVENTION

1. Field of the Invention

The present invention relates to automated operation list generation device, method and program for supporting generation of an automated operation list, which allows automatic execution of a plurality of operations forming a process to generate an image according to a desired purpose.

2. Description of the Related Art

In recent years, a lot of techniques for processing images have been proposed along with development of image processing techniques. Users can sequentially apply a plurality of operations according to the purpose to an image of interest with using these image processing techniques to obtain a desired result. In the medical field, in particular, it is commonly practiced before conducting imaging diagnosis to apply such operations to an image, which is taken with any of various modalities, such as a CT apparatus, a MRI apparatus and an ultrasonographic apparatus, to generate an image in which a desired body part is shown in a visually recognizable manner depending on the purpose of diagnosis.

Techniques for reducing a burden on the user to execute a plurality of operations forming a process to generate an image according to a desired purpose in an order desired by the user have been used. Such techniques involve generating an automated operation list, in which the operations forming the process are registered in a manner to allow the operations to be executed in a desired order, and causing a computer to execute the generated automated operation list.

For example, Japanese Unexamined Patent Publication No. 2005-161032 discloses a method for causing a computer to automatically advance a plurality of operations for image analysis of the heart by storing the operations, which includes operations from setting of a search range for searching the left ventricle of the heart to the final analysis, on the computer and determining requisite minimum items to be inputted by the operator for executing the operations, thereby eliminating the need of input of other items by the operator.

In order to generate such an automated operation list, it is necessary to register the plurality of operations forming the process to generate an image according to the purpose in an accurate order. Further, it is necessary to generate the automated operation list with determining whether each operation in the automated operation list is an operation that does not require input of a processing parameter by the operator during execution of the automated operation list and thus can be automated or an operation that requires input of a processing parameter by the operator during execution of the automated operation list and thus cannot be automated.

However, the content of the operations and the determination as to whether or not each operation can be automated vary depending on the situation of the user. Therefore, if the user does not have enough knowledge about the flow of the operations forming the process according to the purpose, it is difficult to generate the automated operation list. Further, even if the user has enough knowledge about the flow of the operations, it requires troublesome input operations by the user to register each of the operations and processing parameters in the automated operation list to generate the automated operation list, and this requires significant effort and time of the user. In addition, it is difficult to generate the automated operation list for a user who does not have enough knowledge to understand the troublesome input operations for generating the automated operation list.

SUMMARY OF THE INVENTION

In view of the above-described circumstances, the present invention is directed to providing automated operation list generation device, method and program, which reduces troublesome input operations by the user for generating the automated operation list, thereby facilitating generation of the automated operation list.

An aspect of the automated operation list generation device of the invention is an automated operation list generation device for generating an automated operation list, the automated operation list causing a plurality of operations, which form a process to generate an image according to a desired purpose, to be automatically executed in a desired order with using an image analysis application that is able to execute the operations in any order according to input by the user, the device including: inputting means for receiving input of selection of a desired operation from the operations in a desired order and, as necessary, input of a necessary processing parameter for the selected operation; operation information obtaining means for obtaining operation information based on the operation corresponding to the input received by the inputting means, the operation information classifying the operation corresponding to the input into a non-routine operation, which requires input of a processing parameter during execution of the automated operation list, or a routine operation other than the non-routine operation in advance; and automated operation list generating means for generating the automated operation list based on the obtained operation information by registering, if the operation corresponding to the input is a routine operation, the operation corresponding to the input in the automated operation list with associating, as necessary, a necessary processing parameter for the operation with the operation, and if the operation corresponding to the input is a non-routine operation, registering the operation corresponding to the input in the automated operation list.

An aspect of the automated operation list generation method of the invention is an automated operation list generation method implemented by a computer for generating an automated operation list, the automated operation list causing a plurality of operations, which form a process to generate an image according to a desired purpose, to be automatically executed in a desired order with using an image analysis application that is able to execute the operations in any order according to input by the user, the method including: receiving input of selection of a desired operation from the operations in a desired order and, as necessary, input of a processing parameter; obtaining operation information based on the operation corresponding to the received input, the operation information classifying the operation corresponding to the input into a non-routine operation, which requires input of a processing parameter during execution of the automated operation list, or a routine operation other than the non-routine operation in advance; and generating the automated operation list based on the obtained operation information by registering, if the operation corresponding to the input is a routine operation, the operation corresponding to the input in the automated operation list with associating, as necessary, a necessary processing parameter for the operation with the operation, and registering, if the operation corresponding to the input is a non-routine operation, the operation corresponding to the input in the automated operation list.

An aspect of the automated operation list generation program of the invention is an automated operation list generation program for generating an automated operation list, the automated operation list causing a plurality of operations, which form a process to generate an image according to a desired purpose, to be automatically executed in a desired order with using an image analysis application that is able to execute the operations in any order according to input by the user, the program causing a computer to function as: inputting means for receiving input of selection of a desired operation from the operations in a desired order and, as necessary, input of a necessary processing parameter for the selected operation; operation information obtaining means for obtaining operation information based on the operation corresponding to the input received by the inputting means, the operation information classifying the operation corresponding to the input into a non-routine operation, which requires input of a processing parameter during execution of the automated operation list, or a routine operation other than the non-routine operation in advance; and automated operation list generating means for generating the automated operation list based on the obtained operation information by registering, if the operation corresponding to the input is a routine operation, the operation corresponding to the input in the automated operation list with associating, as necessary, a necessary processing parameter for the operation with the operation, and if the operation corresponding to the input is a non-routine operation, registering the operation corresponding to the input in the automated operation list.

The "process to generate an image according to a desired purpose" in the invention encompasses any process that applies a plurality of operations according to a desired purpose to an image of interest. The process includes direct and indirect operations for processing the image of interest, for example, not only operations that alter the image of interest, but also operations such as moving the image of interest on a display screen, storing the image of interest at a predetermined storage location, displaying an edit menu for editing the image of interest, etc.

The image of interest of the process registered in the automated operation list generated by the automated operation list generation device according to the invention may be any image, such as a medical image (for example, a 3D medical image which is reconstructed from a number of slice images taken by tomographic imaging, or the like), an image virtually generated with a CG technique, an image taken with a digital camera, etc. The "image" generated by the "process to generate an image according to a desired purpose" may be a still image or a moving image, and may be any of various known types of images.

In the automated operation list generation device of the invention, the "non-routine operation" refers to an operation which requires input by the user during execution of the automated operation list, and may include, for example, an operation requiring a processing parameter that varies depending on the image. A specific example thereof is an operation to select an object of interest with a shape that varies depending on the image and to delete the object according to the shape thereof.

The "routine operation" refers to an operation other than the non-routine operation, and may include, for example, an operation that does not require input of a processing parameter during execution of the automated operation list or an operation that has a necessary processing parameter for the operation already specified. Further, even when a certain operation requires a processing parameter that varies depending on the image, if the processing parameter can be specified, according to a predetermined function or rule, from a result of processing of the image of interest obtained by sequentially executing the operations in the automated operation list, then, such an operation may be included in the routine operation since input by the user can be omitted during execution of the automated operation list. For example, an operation to enlarge or reduce the image to a predetermined size, an operation to select, from files forming a moving image, files in a predetermined, temporally continuous time range from a point of time at X % (relative to the entire imaging time of the moving image) from the start of imaging to a point of time at Y % (relative to the entire imaging time of the moving image) before the end of imaging, etc., may be included in the routine operations.

The "processing parameter" refers to a parameter used to execute each operation. For example, the processing parameter may be a parameter inputted by manual operation by the user, such as a certain reduction factor, a numerical value, specification of a range, or a destination address of a file.

In the automated operation list generation device of the invention, the inputting means may be formed by any of various known types of input devices, such as a mouse, a keyboard, a touch panel and a microphone, that can receive input by the user. The description "receiving selection of a desired operation . . . and, as necessary, input of a necessary processing parameter for the selected operation" refers to receiving necessary input for executing each operation forming the process to generate an image according to a desired purpose conducted by the user. For example, if an operation to cut a part of the image is conducted, an input made by mouse click on a cut range selection button corresponds to the input of selection of an operation, and an input to select the cut range corresponds to the input of a processing parameter. If an operation to close an operation window is conducted, for example, an input to select an item to close the operation window from the menu of the operation window corresponds to the input of selection of an operation. In this case, no processing parameter is necessary to close the operation window and thus no processing parameter is inputted.

The operation of "registering, . . . in the automated operation list with associating a necessary processing parameter for the operation with the operation" may be achieved in any of various manners as long as each processing parameter is associated with a corresponding operation in the automated operation list in a referable manner. For example, each processing parameter may be directly registered in the automated operation list, or information for specifying each processing parameter may be registered in the automated operation list.

The automated operation list generation device according to the invention may further include changing means for changing a non-routine operation in the generated automated operation list into a routine operation based on further input received by the inputting means. Further, the changing means may be able to change a routine operation in the generated automated operation list into a non-routine operation based on further input received by the inputting means.

When a non-routine operation in the automated operation list is changed into a routine operation, the changing means may specify, as necessary, a necessary processing parameter for the non-routine operation during execution of the automated operation list. Further, the changing means may be able to change a non-routine operation in the automated operation list into a routine operation, and vice versa, during execution of the automated operation list, so that the user can determine whether or not each operation should be handled as a routine operation based on the result of execution of the operation.

The automated operation list generation device according to the invention may further include executing means for causing the operations registered in the automated operation list to be automatically executed in an order of registration of the operations in the automated operation list, wherein, if an operation to be executed is a routine operation, the routine operation is automatically executed with using a processing parameter associated with the routine operation registered in the automated operation list, and if an operation to be executed is a non-routine operation, input of selection by the user as to whether to execute or skip the non-routine operation is received, and then if it is selected to execute the non-routine operation, the non-routine operation is executed.

The automated operation list generating means may also register, if the operation corresponding to the input is a non-routine operation, the operation in the automated operation list with associating a necessary processing parameter for the operation with the operation, and the executing means may receive, if the operation to be executed is a non-routine operation, input of selection by the user as to whether to obtain the processing parameter registered in the automated operation list or to receive input of the processing parameter by the user, and cause the non-routine operation to be executed with using the selected processing parameter.

The executing means may be able to selectively execute part or all of the operations registered in the automated operation list according to selection by the user. Further, the executing means may execute any of the operations registered in the automated operation list in a stepwise manner, or may automatically execute any of the operations registered in the automated operation list.

At least one of the automated operation list generating means and the changing means of the automated operation list generation device according to the invention may be able to set in the automated operation list whether or not to skip each non-routine operation registered in the automated operation list during execution of the automated operation list, and the executing means may be adapted not to execute the non-routine operation which is set to be skipped during execution of the automated operation list.

The automated operation list can be set to skip all or part of the non-routine operations registered in the automated operation list. For example, all the operations registered in the automated operation list may be automatically executed with skipping all the non-routine operations according to setting by the user.

The automated operation list generation device according to the invention may further include display controlling means for displaying the automated operation list on a display device such that the operation being executed is identifiable synchronously with execution of each operation in the automated operation list. Further, the display controlling means may display an image of result of each operation on the display device synchronously with execution of each operation in the automated operation list.

The automated operation list may be displayed in any manner as long as the individual operations registered in the automated operation list are displayed. For example, the automated operation list may be displayed by displaying simple descriptions or keywords representing the outlines of the individual operations registered in the automated operation list, or by displaying operation IDs of the individual operations or pictures representing the individual operations. In order to display the automated operation list such that the user can easily understand the operations that require input by the user, the classification of each operation (i.e., whether it is a routine operation or a non-routine operation) may be displayed in an identifiable manner.

Display the operation being executed or the classification of each operation in an identifiable manner may be achieved in any known manner. For example, a text representing the operation being executed in the displayed automated operation list may be displayed in an identifiable color and/or size, or an index that indicates the operation being executed in an identifiable manner may be displayed on the displayed automated operation list. Further, a text representing each non-routine operation (or routine operation) in the displayed automated operation list may be displayed in an identifiable color and/or size, or an index that indicates each non-routine operation (or routine operation) in the displayed automated operation list may be displayed in an identifiable manner.

The automated operation list may show all the operations registered in the automated operation list at once, or may display a consecutive part of the operations registered in the automated operation list. Further, synchronously with the progress of the operations in the automated operation list, a keyword or description representing the currently executed operation among the operations registered in the automated operation list may be displayed in turn.

In order to facilitate the user's understanding of the operations registered in the automated operation list and the image of result of each operation in an associated manner, the display controlling means may optionally display, on the display device, the automated operation list showing the operation being executed in an identifiable manner and the image of result of the operation being executed such that the user can compare the automated operation list and the image of result with each other synchronously with the progress of the operations in the automated operation list. For example, the display controlling means may display the automated operation list showing the operation being executed in an identifiable manner and the image of result of the operation being executed side by side on the same display to facilitate visual recognition by the user.

The automated operation list generation device according to the invention may further include explanation information generating means for storing explanation information in an editable manner, the explanation information explaining each operation in the automated operation list, wherein the display controlling means may display the explanation information on the display device synchronously with execution of each operation in the automated operation list.

Optionally, the display controlling means may display the explanation information corresponding to the operation being executed synchronously with the progress of the operations in the automated operation list such that the user can compare the explanation information with the automated operation list which shows the operation being executed in an identifiable manner. For example, the automated operation list showing the operation being executed in an identifiable manner and the explanation information corresponding to the operation being executed may be displayed side by side on a single display to facilitate visual recognition by the user. Further optionally, in order to facilitate the user's understanding of the operations registered in the automated operation list, the image of result of each operation and the explanation information corresponding to each operation in an associated manner, the display controlling means may display the automated operation list showing the operation being executed in an identifiable manner, the image of result of the operation being executed and the explanation information corresponding to the operation being executed synchronously with the progress of the operations in the automated operation list such that the user can compare them with each other.

Further, the executing means of the automated operation list generation device according to the invention may be able to set to start the execution of the automated operation list in any of various known manners. For example, the automated operation list may be executed in response to activation of the image analysis application, or the executing means may execute the automated operation list in response to selection of a medical image of interest.

According to the automated operation list generation device, method and program of the invention, input of selection of each operation in a desired order by the user is received and, as necessary, input of a processing parameter by the user is received, and the operation information, which classifies each operation corresponding to the input into a non-routine operation, which requires input of a processing parameter during execution of the automated operation list, or a routine operation other than the non-routine operation in advance, is obtained based on the operation corresponding to the received input. Then, the automated operation list is generated based on the obtained operation information by registering, if the operation corresponding to the input is a routine operation, the operation corresponding to the input in the automated operation list with associating, as necessary, a necessary processing parameter for the operation with the operation, and registering, if the operation corresponding to the input is a non-routine operation, the operation corresponding to the input in the automated operation list. Thus, the user only needs to execute a plurality of operations, which form a process to generate an image according to a desired purpose, in a desired order to generate the automated operation list, in which each operation forming the process to generate an image according to a desired purpose is classified into the routine operation or the non-routine operation and the necessary processing parameter for each routine operation is associated with the routine operation, as necessary. This reduces the burden of troublesome operations of determining whether or not each operation forming the process to generate an image according to a desired purpose is a routine operation and specifying, as necessary, a necessary processing parameter for each routine operation during generation of the automated operation list.

In the case where the changing means for changing a non-routine operation in the generated automated operation list into a routine operation based on further input received by the inputting means is further provided, changing of the classification of each operation (i.e., whether it is a routine operation or a non-routine operation) in the automated operation list generated according to a desired purpose can be achieved easily and flexibly, thereby facilitating generation of the automated operation list as required by the user.

Further, in the case where the changing means of the automated operation list generation device of the invention can change a routine operation in the generated automated operation list into a non-routine operation based on further input received by the inputting means, changing of the classification of each operation (i.e., whether it is a routine operation or a non-routine operation) in the automated operation list generated according to a desired purpose can be achieved easily and flexibly, thereby facilitating generation of the automated operation list as required by the user.

In the case where the automated operation list generation device of the invention further includes the executing means for automatically executing each operation registered in the automated operation list in the order of registration of the operations in the automated operation list, where if the operation to be executed is a routine operation, the routine operation is automatically executed with using an associated processing parameter registered in the automated operation list, and if the operation to be executed is a non-routine operation, input by the user as to whether to execute or skip the non-routine operation is received, and then, if it is selected to execute the non-routine operation, the non-routine operation is executed, the user only needs to input selection as to whether to execute or skip each non-routine operation during execution of the automated operation list, and thus can easily execute the plurality of operations for generating a desired image based on the generated automated operation list.

In the case where the automated operation list generating means also registers, if the operation corresponding to the input is a non-routine operation, the operation corresponding to the input in the automated operation list with associating a necessary processing parameter for the operation with the operation, and the executing means receives, if the operation to be executed is a non-routine operation, input of selection by the user as to whether to obtain the processing parameter registered in the automated operation list or to receive input of the processing parameter by the user, and causes the non-routine operation to be executed with using the selected processing parameter, input of the processing parameter for the non-routine operation by the user during execution of the automated operation list can be omitted based on the generated automated operation list if the processing parameter registered in the automated operation list is used, thereby facilitating execution of the plurality of operations for generating a desired image.

In the case where at least one of the automated operation list generating means and the changing means according to this embodiment can set, in the automated operation list, whether or not to skip each non-routine operation registered in the automated operation list during execution of the automated operation list, and the executing means does not execute the non-routine operation which is set to be skipped during execution of the automated operation list, input by the user as to whether to execute or skip each non-routine operation during execution of the automated operation list L can be omitted for the non-routine operation which is set to be skipped, and thus the plurality of operations for generating a desired image can be executed easily based on the generated automated operation list.

In the case where the automated operation list generation device of the invention further includes the display controlling means for displaying the automated operation list on a display device such that the operation being executed is identifiable synchronously with execution of each operation in the automated operation list is provided, understanding of the operations for generating a desired image registered in the automated operation list and the order of automatic execution of the operations is facilitated.

In the case where the display controlling means of the automated operation list generation device of the invention displays the image of result of each operation on the display device synchronously with execution of each operation in the automated operation list, understanding of the operations for generating a desired image registered in the automated operation list is facilitated.

In the case where the automated operation list generation device of the invention further includes the explanation information generating means for storing the explanation information, which explains each operation in the automated operation list, in an editable manner, and the display controlling means displays the explanation information on the display device synchronously with execution of each operation in the automated operation list, even a third person who is not familiar with the operations for generating a desired image can execute the automated operation list with referring to the explanation information, such as the order, the purpose and/or precautions of the operations forming the automated operation list. This helps the user to understand the operations for generating a desired image registered in the automated operation list and to use the automated operation list.

In the case where the executing means of the automated operation list generation device of the invention executes the automated operation list in response to activation of the image analysis application, input by the user to activate the execution of the automated operation list can be omitted, thereby facilitating execution of the automated operation list.

In the case where the executing means of the automated operation list generation device of the invention executes the automated operation list in response to selection of a medical image of interest, input by the user to activate the execution of the automated operation list can be omitted, thereby facilitating execution of the automated operation list.

BRIEF DESCRIPTION OF THE DRAWINGS

FIG. 2 is a diagram illustrating an example of an operation information table of the first embodiment, FIG. 3 is a diagram illustrating an example of an automated operation list of the first embodiment.

DESCRIPTION OF THE PREFERRED EMBODIMENTS

Hereinafter, embodiments of automated operation list generation device, automated operation list generation program and automated operation list generation method of the present invention will be described in detail with reference to the drawings, with using a plurality of operations forming a process to generate an image according to the purpose of imaging diagnosis at a medical institution as an example.

Figure 1:
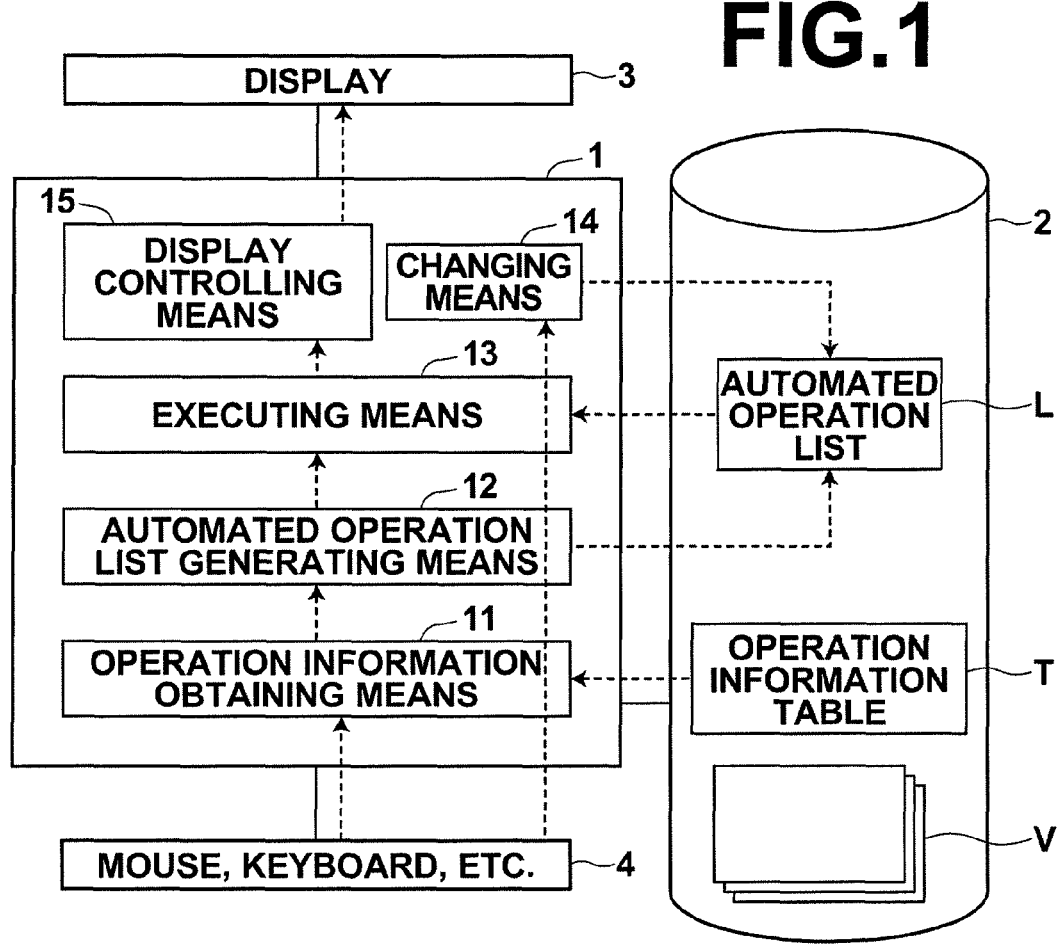
FIG. 1 is a diagram illustrating the schematic configuration of an automated operation list generation device according to a first embodiment.

FIG. 1 shows the schematic configuration of the automated operation list generation device, which is implemented by installing the automated operation list generation program on a workstation used by a doctor. The automated operation list generation device includes, as a standard configuration of a workstation, a processing unit 1 including a processor and a memory (which are not shown in the drawing) and an input device (inputting means) 4, such as a mouse, keyboard, etc. The automated operation list generation device also includes a storage 2, such as a HDD (Hard Disk Drive) or SSD (Solid State Drive), and a display 3 connected to the automated operation list generation device.

The automated operation list generation program and data (such as tables described later) referenced by the automated operation list generation program are stored in the storage 2 during the installation and are loaded in the memory when the program is activated. The automated operation list generation program prescribes, as operations to be executed by the CPU, an operation information obtaining operation, an automated operation list generating operation, an executing operation, a changing operation and a display controlling operation. When the CPU executes each of the above operations according to the prescription of the program, the general-purpose workstation functions as an input device 4, an operation information obtaining means 11, an automated operation list generating means 12, an executing means 13, a changing means 14 and a display controlling means 15.

The storage 2 stores volume data transferred from an examination department, where imaging is conducted, or volume data V (3D image V) obtained by searching a database. The volume data V to be obtained may be volume data that is taken with any of various known modalities, such as a CT apparatus. The storage 2 stores information necessary for each operation, such as an operation information table T, an automated operation list L and an explanation information table C, which will be described later.

The inputting means 4 may be formed by any of various known types of input devices, such as a mouse, a keyboard, a touch panel and a microphone, that can receive input by the user. The input device 4 (inputting means 4) has a function to receive selection of operations in a desired order by the user, and receive, as necessary, input of processing parameters necessary for the selected operations. Namely, the input device 4 receives necessary input for executing each operation forming the process to generate an image according to a desired purpose conducted by the user. For example, if an operation to cut a part of the image is conducted, an input made by mouse click on a cut range selection function button corresponds to the input of selection of operations, and an input to select the cut range corresponds to the input of processing parameters. If an operation to close an operation window is conducted, for example, an input to select an item to close the operation window from the menu of the operation window corresponds to the input of selection of operations. In this case, no processing parameter is necessary to close the operation window and thus no processing parameter is inputted.

The operation information obtaining means 11 has a function to obtain, based on each operation corresponding to the input received by the input device 4, operation information, which classifies each operation corresponding to the input into a non-routine operation, which requires input of a processing parameter during execution of the automated operation list, or a routine operation other than the non-routine operation in advance. In this embodiment, the operation information classifying each operation corresponding to the input into the non-routine operation, which requires input of a processing parameter during execution of the automated operation list, or the routine operation other than the non-routine operation in advance, is obtained with referencing the operation information table T, which is prepared in the storage 2 in advance. FIG. 2 is a diagram illustrating an example of the operation information table T in the first embodiment. In this embodiment, as shown in FIG. 2, the operation information table T contains, for each operation carried out by the analysis application, an operation ID, a comment describing the outline of the operation, classification of whether the operation is a non-routine operation or a routine operation, and a necessary processing parameter for the operation. Before the automated operation list is generated, the processing parameters are set at initial values given in advance. It should be noted that, although the same items with the same contents may be defined in the operation information table T for each system in the medical institution, the items and the contents thereof defined in the operation information table T can arbitrarily be set by each user in this embodiment.

It should be noted that the "non-routine operation" refers to an operation which requires input by the user during execution of the automated operation list, and may include, for example, an operation requiring a processing parameter that varies depending on the image, as shown in FIG. 2. One example thereof is an operation to select an object of interest with a shape that varies depending on the image and to delete the object according to the shape thereof. The "routine operation" refers to an operation other than the non-routine operation, and may include, for example, an operation that does not require input of a processing parameter during execution of the automated operation list or an operation that has a necessary processing parameter for the operation already specified, as shown in FIG. 2. Further, even when a certain operation requires a processing parameter that varies depending on the image, if the processing parameter can be specified, according to a predetermined function or rule, from a result of processing of the image of interest obtained by sequentially executing the operations in the automated operation list, then, such an operation may be included in the routine operation since input by the user can be omitted during execution of the automated operation list. For example, an operation to enlarge or reduce the image to a predetermined size, an operation to select, from files forming a moving image, files in a predetermined, temporally continuous time range from a point of time at X % (relative to the entire imaging time of the moving image) from the start of imaging to a point of time at Y % (relative to the entire imaging time of the moving image) before the end of imaging, etc., may be included in the routine operations.

The "processing parameter" refers to a parameter used to execute each operation. For example, the processing parameter may be a parameter inputted by manual operation by the user, such as a certain reduction factor, a numerical value, specification of a range, or a destination address of a file.

Based on the obtained operation information, if the operation corresponding to the input is a routine operation, the automated operation list generating means 12 registers the operation corresponding to the input with associating, as necessary, a necessary processing parameter therewith in the automated operation list L, and if the operation corresponding to the input is a non-routine operation, the automated operation list generating means 12 registers the operation corresponding to the input in the automated operation list L, thereby generating the automated operation list. The automated operation list L may be generated in an XML format, for example. FIG. 3 is a diagram illustrating an example of the automated operation list L in the first embodiment. As shown in FIG. 3, the automated operation list L contains, for each operation forming the process according to a desired purpose, an operation ID, a comment describing the outline of the operation, classification of whether the operation is a non-routine operation or a routine operation, and a necessary processing parameter for the operation, which are associated with the operation. It is assumed here that, for each processing parameter of each operation, whether or not the parameter is to be updated based on input by the user is set by the user when the automated operation list is generated.

The processing parameters may be associated with the operations in the automated operation list in any of various manners. For example, the processing parameters may be directly registered in the automated operation list, or information for specifying each processing parameter may be registered in the automated operation list.

The executing means 13 causes the operations registered in the automated operation list L to be automatically executed in order. If the operation is a routine operation, an associated processing parameter registered in the automated operation list L is fed to execute the operation based on the processing parameter. If the operation is a non-routine operation, the executing means 13 receives input of selection by the user as to whether the operation is executed based on an associated processing parameter registered in the automated operation list L, the operation is executed based on a processing parameter inputted by the user during execution of the automated operation list L or the operation is skipped, and executes or skips the operation according to the selection.

It should be noted that, according to the setting of skip for each non-routine operation registered in the automated operation list L, the executing means 13 may automatically execute the automated operation list L from the start to the end with skipping all the non-routine operations, or the executing means 13 may automatically execute a part of the automated operation list L with skipping a part of the non-routine operations, for example.

Further, in this embodiment, the automated operation list generating means 12 also registers the operation corresponding to the input in the automated operation list with associating a necessary processing parameter therewith if the operation corresponding to the input is a non-routine operation. Then, the executing means 13 receives input of selection by the user as to whether to obtain an associated processing parameter registered in the automated operation list L or to receive input of a processing parameter by the user if the operation to be executed is a non-routine operation, and causes the non-routine operation to be executed with suing the selected processing parameter.

It should be noted that the executing means 13 is able to selectively execute part or all of the operations registered in the automated operation list L according to selection by the user, to execute any of the operations registered in the automated operation list in a stepwise manner, and to automatically execute any of the operations registered in the automated operation list.

Further, in the case where the automated operation list L which is generated by receiving execution of each non-routine operation during generation of the automated operation list L is automatically executed, the executing means 13 obtains, for each non-routine operation registered in the automated operation list L, a necessary processing parameter for the non-routine operation by receiving input by the user, as necessary.

The changing means 14 changes the generated automated operation list L based on further input received by the input device 4. In this embodiment, the changing means 14 can change a non-routine operation in the generated automated operation list L into a routine operation, and can change a routine operation in the automated operation list L into a non-routine operation. Further, the changing means 14 can change the content of each item in the automated operation list L as required by the user.

In addition, the automated operation list generating means 12 or the changing means 14 can set, for each non-routine operation registered in the automated operation list L, whether or not to skip the operation during execution of the automated operation list. Then, the executing means 13 does not execute the non-routine operation which is set to be skipped during execution of the automated operation list.

In this embodiment, when a certain non-routine operation in the automated operation list L is changed into a routine operation, the changing means 14 specifies a necessary processing parameter for the operation during execution of the automated operation list, as necessary. Further, in this embodiment, when the executing means 13 executes the automated operation list L, the changing means 14 can change a routine operation into a non-routine operation and a non-routine operation into a routine operation in the automated operation list L.

Figure 4:
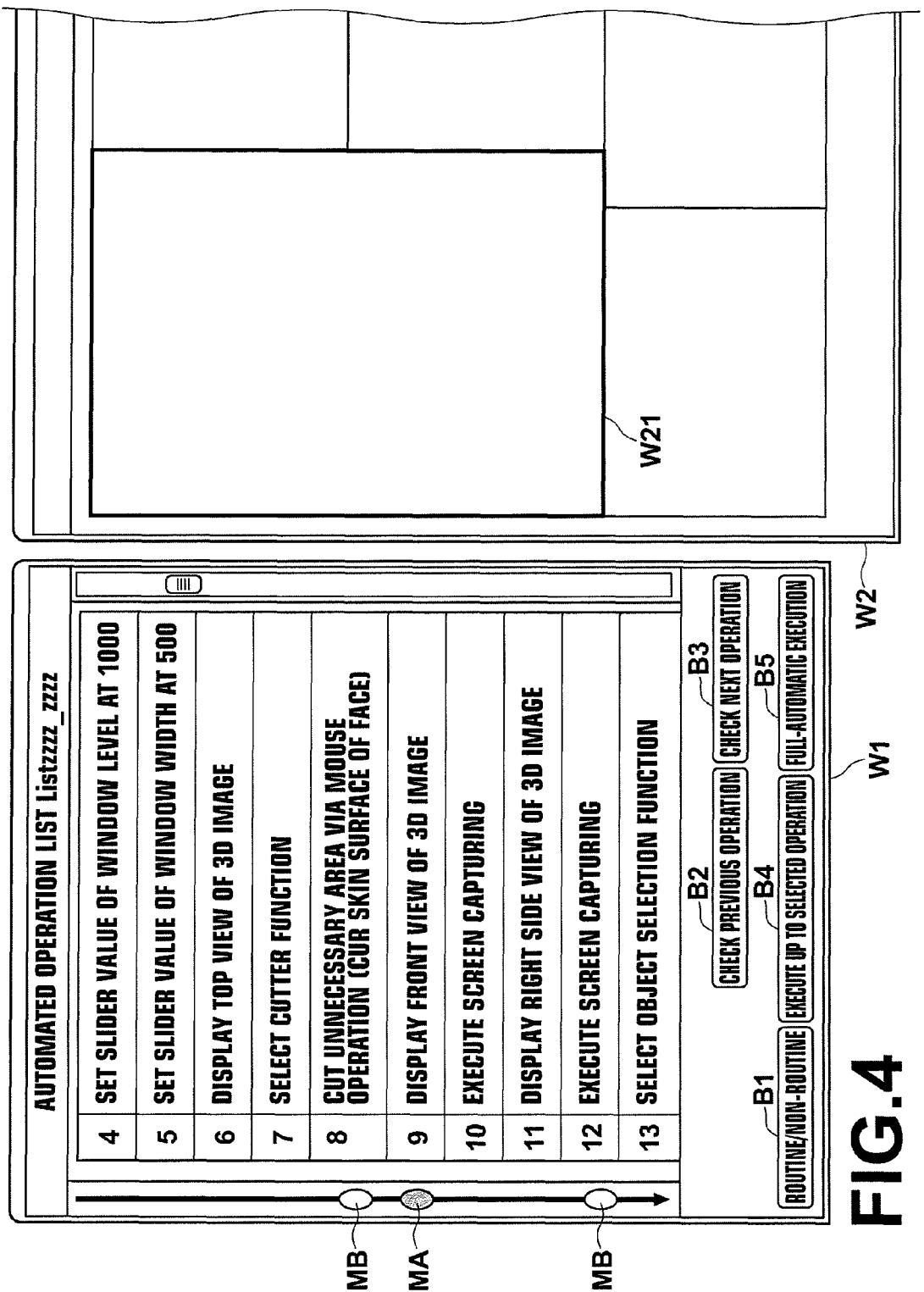
FIG. 4 is a diagram illustrating an example of an automated operation list in an automated operation list generation method of the first embodiment.

FIG. 4 shows an example of display of the automated operation list L shown in FIG. 3. In the example shown in FIG. 4, an analysis application window W2, which is a work space for the activated analysis application, and an automated operation list display window W1, where the automated operation list L is displayed, are displayed on a display screen. The analysis application window W2 contains various windows, including a display window W21 for displaying the image of interest.

As shown in FIG. 4, the display controlling means 15 causes the display device 3 to display an image of result of each operation synchronously with execution of each operation in the automated operation list L, and causes the display device 3 to display the automated operation list L such that the operation being executed is identifiable synchronously with execution of each operation in the automated operation list L. It should be noted that the image of result of each operation may be any image that represents a result of execution of each operation in the automated operation list L. For example, if the operation is to close the window displaying the image of interest, the image of result may represent the display screen after the window is closed.

The automated operation list L may be displayed in any manner as long as the individual operations registered in the automated operation list L are displayed. For example, the automated operation list may be displayed by displaying simple descriptions or keywords representing the outlines of the individual operations registered in the automated operation list, or by displaying the operation IDs of the individual operations or pictures representing the individual operations. In order to display the automated operation list such that the user can easily understand the operations that require input by the user, the classification of each operation (i.e., whether it is a routine operation or a non-routine operation) may be displayed in an identifiable manner.

Display the operation being executed or the classification of each operation in an identifiable manner may be achieved in any known manner. For example, a text representing the operation being executed in the displayed automated operation list may be displayed in an identifiable color and/or size, or an index that indicates the operation being executed in an identifiable manner may be displayed on the displayed automated operation list. Further, a text representing each non-routine operation (or routine operation) in the displayed automated operation list may be displayed in an identifiable color and/or size, or an index that indicates each non-routine operation (or routine operation) in the displayed automated operation list may be displayed in an identifiable manner.

The automated operation list L may show all the operations registered in the automated operation list at once, or may display a consecutive part of the operations registered in the automated operation list L. Further, synchronously with the progress of the operations in the automated operation list, a keyword or description representing the currently executed operation among the operations registered in the automated operation list L may be displayed in turn.

In order to facilitate the user's understanding of the operations registered in the automated operation list L and the image of result of each operation in an associated manner, the display controlling means 15 may optionally display, on the display device 3, the automated operation list L showing the operation being executed in an identifiable manner and the image of result of the operation being executed such that the user can compare the automated operation list L and the image of result with each other synchronously with the progress the operations in the automated operation list L. In this embodiment, the display controlling means 15 displays the automated operation list L showing the operation being executed in an identifiable manner and the image of result of the operation being executed side by side on the same display 3 to facilitate visual recognition by the user.

Figure 5:
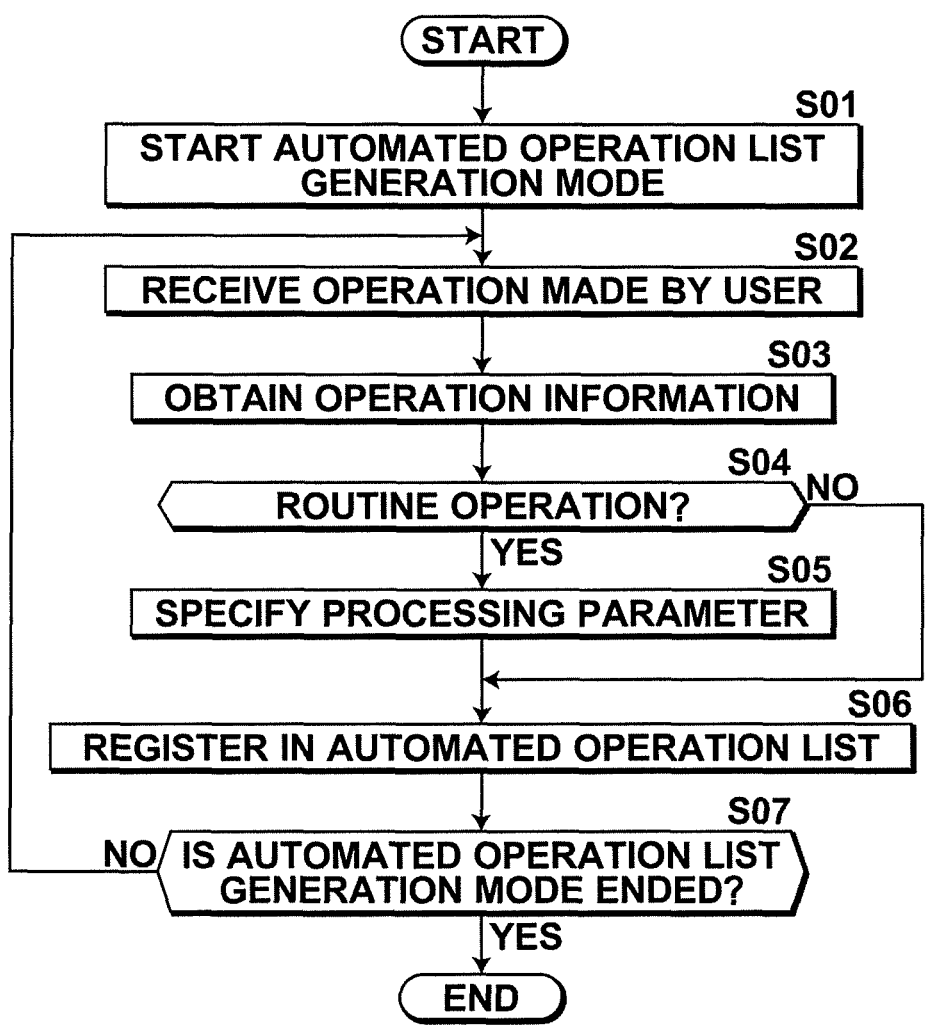
FIG. 5 is a flow chart illustrating the flow of the automated operation list generation method of the first embodiment (the stage of generating the automated operation list)

FIG. 5 is a flow chart illustrating the flow of an automated operation list generation method of the first embodiment (the stage of generating the automated operation list). The automated operation list generation method of this embodiment is described with reference to FIGS. 2 to 5.

When the automated operation list generation device detects that a predetermined automated operation list generation function is selected from a selection menu, the automated operation list generation device prompts the user to select or input necessary information for specifying volume data. When the volume data is specified via the operation by the user, the corresponding volume data is loaded from the storage 2 into the memory.

It is assumed in this example that a blood vessel area in the head has been imaged with an MRI apparatus in an examination of a certain patient, and a three-dimensional MRA image containing information of the cerebral artery has been obtained. In this embodiment, an image analysis application, which is able to execute a plurality of operations forming a process according to the purpose of generating desired captured images of the MRA image and storing the generated captured images in a predetermined server in an arbitrary order according to input by the user, is activated, and when the identifier of the patient and the examination date are inputted, the corresponding volume data is loaded in the memory, and the automated operation list generation process of the invention is executed.

First, prior to carrying out the automated operation list generation method of this embodiment, the operation information table T is generated in advance on an arbitrary workstation, and the generated operation information table T is stored in the storage 2 via a network or a portable storage medium.

As shown in FIG. 2, the operation information table T contains, for each operation executed by the analysis application, the operation ID, the comment describing the outline of the operation, the classification of whether the operation is a non-routine operation or a routine operation and the necessary processing parameter for the operation. Before the automated operation list is generated, the processing parameters are set at initial values given in advance.

Now, the automated operation list generation method of this embodiment is described according to FIG. 5.

First, when the user clicks, with the mouse 4, on an automated operation list generation button, which is displayed on a screen of a cerebral artery analysis application, this click is detected and an automated operation list generation mode is started (S01). As shown in FIG. 3, this embodiment shows an example where a plurality of operations to generate a plurality of captured images, which show blood vessels of the head viewed from predetermined angles, from the MRA image and to store the generated captured images in a predetermined server are registered in the automated operation list.

The inputting means 4 corresponds to the input device 4 in this embodiment, which receives input of selection of each operation in a desired order by the user and receives, as necessary, input of a necessary processing parameter for the selected operations by the user (S02).

Then, based on each operation corresponding to the input received by the input device 4, the operation information obtaining means 11 obtains the operation information, which classifies each operation corresponding to the input into the non-routine operation, which requires input of a processing parameter during execution of the automated operation list, or the routine operation other than the non-routine operation in advance. In this embodiment, the operation information obtaining means 11 first obtains the operation information table T from the storage 2 and stores it in the memory. Then, each operation inputted via the input device 4 is detected, and the corresponding operation information is obtained from the operation information table T (S03). In the example shown in FIG. 3, first, operations made by the user with the mouse 4 to select the window W21, which displays the 3D image V, and to specify the 3D image in the selected window W21 as the image of interest are detected, and the corresponding pieces of operation information are obtained from the operation information table T.

Based on the obtained operation information, the automated operation list generating means 12 generates the automated operation list by registering, if the operation corresponding to the input is a routine operation, the operation corresponding to the input with associating, as necessary, a necessary processing parameter for the operation therewith in the automated operation list L, and registering, if the operation corresponding to the input is a non-routine operation, the operation corresponding to the input in the automated operation list L. In this embodiment, the automated operation list generating means 12 references the operation corresponding to the input and the operation information table T to determine whether the inputted operation is a routine operation or a non-routine operation based on the operation information corresponding to the inputted operation (S04). Then, if the specified operation is a routine operation (YES at S04), a necessary processing parameter for executing the routine operation is specified based on the detected operation by the user (S05). Then, the specified operation and the processing parameter for the specified operation are associated with each other and are registered in the automated operation list L (S06).

For example, in the example shown in FIG. 3, the operation to select a 3D image is a routine operation, and therefore information for specifying the 3D image to be selected is specified as the processing parameter. Then, the automated operation list generating means 12 registers the specified "operation to select a 3D image" and the processing parameter in the automated operation list L.

In this example, information for specifying the type of display window which displays the 3D image of interest is registered in the automated operation list L as the processing parameter for the "operation to select a 3D image". During execution of the automated operation list L, the executing means 13 obtains the ID of an image displayed in the specified display window as the ID of the image of interest of the automated operation list L and executes each operation. Since a different 3D image is set as the image of interest each time the automated operation list L is executed, it may be considered to set the "operation to select a 3D image" as the non-routine operation and execute the operation with manual operation by the user. However, the image of interest can indirectly be specified during execution of the automated operation list L by specifying the type of the display window which displays the 3D image of interest, and thus the "operation to select a 3D image" can be executed as the routine operation.

It should be noted that the processing parameter may be specified so as to select an image at a predetermined position on the display screen. The processing parameter may be specified with using any of various known methods.

On the other hand, if the specified operation is a non-routine operation (NO at S04), the specified operation is registered in the automated operation list L (S06).

For example, in the case where an operation to cut the skin surface of the face is specified via operation of the mouse, the operation to cut the skin surface of the face is registered in the automated operation list L. It should be noted that, for the non-routine operations, whether or not a processing parameter is associated with each non-routine operation to be registered in the automated operation list L is not essential. However, in this embodiment, a processing parameter used to execute each non-routine operation when the non-routine operation is specified is associated with the non-routine operation to be registered in the automated operation list L. In this example, information for specifying a cut area, such as coordinates in the image, is associated with the operation to cut the skin surface of the face as the processing parameter to be registered in the automated operation list L.

The automated operation list generating means 12 repeats the operation in S02 to S06 while the automated operation list generation mode continues (NO at S07) until the user clicks on the automated operation list generation button displayed on the screen of the cerebral artery analysis application. Namely, the series of operations, where the inputting means 4 receives input of each operation forming the process according to the purpose inputted by the user in a desired order, the operation information obtaining means 11 detects each operation inputted by the user in the order of execution to obtain the operation information, and the automated operation list generating means 12 registers each operation and a necessary processing parameter in the automated operation list L in the order of execution, are repeated.

Now, the manual input operations by the user and the outline of the operations in the example shown in FIG. 4 are described. As the first operation, the user clicks on the image display window W21, which displays the 3D image, with the mouse 4, and the image display window is displayed in an identifiable manner (for example, a white frame is provided around the image display window). As the second operation, the user selects, via the input device 4, MIP display as the display method for the 3D image V, and the 3D image V is displayed in the manner of MIP display. As the third operation, the user selects, via the input device 4, a Window Width/Level function to cause a Window Width/Level setting screen to be displayed. As the fourth operation, the user specifies, via the input device 4, a slider value of 1000 for the Window Width on the Window Width/Level setting screen. As the fifth operation, the user specifies, via the input device 4, a slider value of 500 for the Window Level on the Window Width/Level setting screen. As the sixth operation, the user selects, via the input device 4, a top view display button, which is displayed on the image in a selectable manner, to cause the image to rotate into a predetermined orientation, thereby displaying the top view of the 3D image V. As the seventh operation, the user selects a cutter function via the input device 4. As the eighth operation, the user cuts the skin surface of the face, which is an unnecessary area, by operating the mouse of the input device 4. As the ninth operation, the user selects, via the input device 4, a front view display button, which is displayed on the image in a selectable manner, to cause the image to rotate into a predetermined orientation, thereby displaying the front view of the 3D image V. As the tenth operation, the user presses, via the input device 4, a capture button, which is displayed on the image in a selectable manner. This causes a front view image of the cerebral artery to be transferred to a capture box, which is a predetermined area of a storage for storing the captured images. As the eleventh operation, the user selects, via the input device 4, a side view button, which is displayed on the image in a selectable manner, to cause the image to rotate into a predetermined orientation, thereby displaying the (right) side view of the 3D image V. As the twelfth operation, the user presses the capture button via the input device 4. This causes a side view image of the cerebral artery to be obtained in the memory and displayed on the image. As the thirteenth operation, the user selects, via the input device 4, an object selection function, which is displayed on the image in a selectable manner. This function automatically extracts an object containing a position selected by the user and displays only the extracted object on the screen. As the fourteenth operation, the user selects the object (cerebral artery) via the input device 4. This causes the cerebral artery, which is the object containing the position selected by the user, to be automatically extracted, and only the extracted cerebral artery to be displayed on the screen. As the fifteenth operation, the user selects the front view display button via the input device 4 to cause the image to rotate into a predetermined orientation, thereby displaying the front view of the 3D image V. As the sixteenth operation, the user presses the capture button via the input device 4. This causes a front view image of the cerebral artery to be transferred to the capture box. As the seventeenth operation, the user selects the side view button via the input device 4 to cause the image to rotate into a predetermined orientation, thereby displaying the (right) side view of the 3D image V. As the eighteenth operation, the user presses the capture button via the input device 4. This causes a side view image of the cerebral artery to be transferred to the capture box. As the nineteenth operation, the user causes, via the input device 4, the capture box to be displayed. At this time, the capture box stores two front view images and two side view images obtained by the above operations. As the twentieth operation, the user specifies, via the input device 4, "image storing server A" as a transfer destination address provided at the capture box. As the twenty-first operation, the user executes, via the input device 4, transfer of all the images stored in the capture box.

When the user again clicks with the mouse 4 on the automated operation list generation button displayed on the screen of the cerebral artery analysis application, the automated operation list generating means 12 detects this click and the automated operation list generation mode ends (YES at S07). The user provides the thus generated automated operation list L with an appropriate file name and stores the automated operation list L in the storage 2.

In this manner, the automated operation list L, as shown in FIG. 3, is generated. The automated operation list L contains, for each of the operations forming the process to generate an image according to a desired purpose, the operation ID, the comment describing the outline of the operation, the classification of whether the operation is a non-routine operation or a routine operation and the necessary processing parameter for the operation, which are associated with the operation. The types and contents of the items to be associated with each operation in the automated operation list L can arbitrarily be set by each user.

Figure 6:
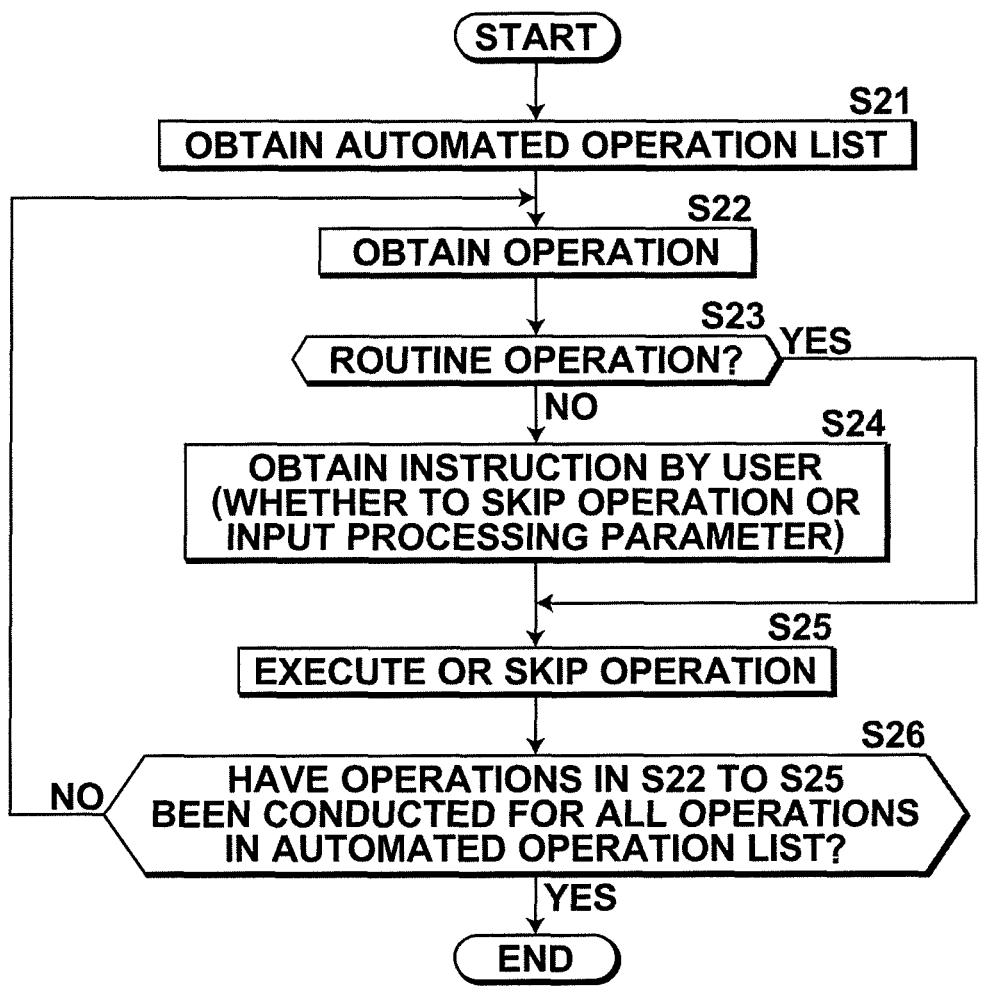
FIG. 6 is a flow chart illustrating the flow of the automated operation list generation method of the first embodiment (the stage of executing the automated operation list)
Figure 7:
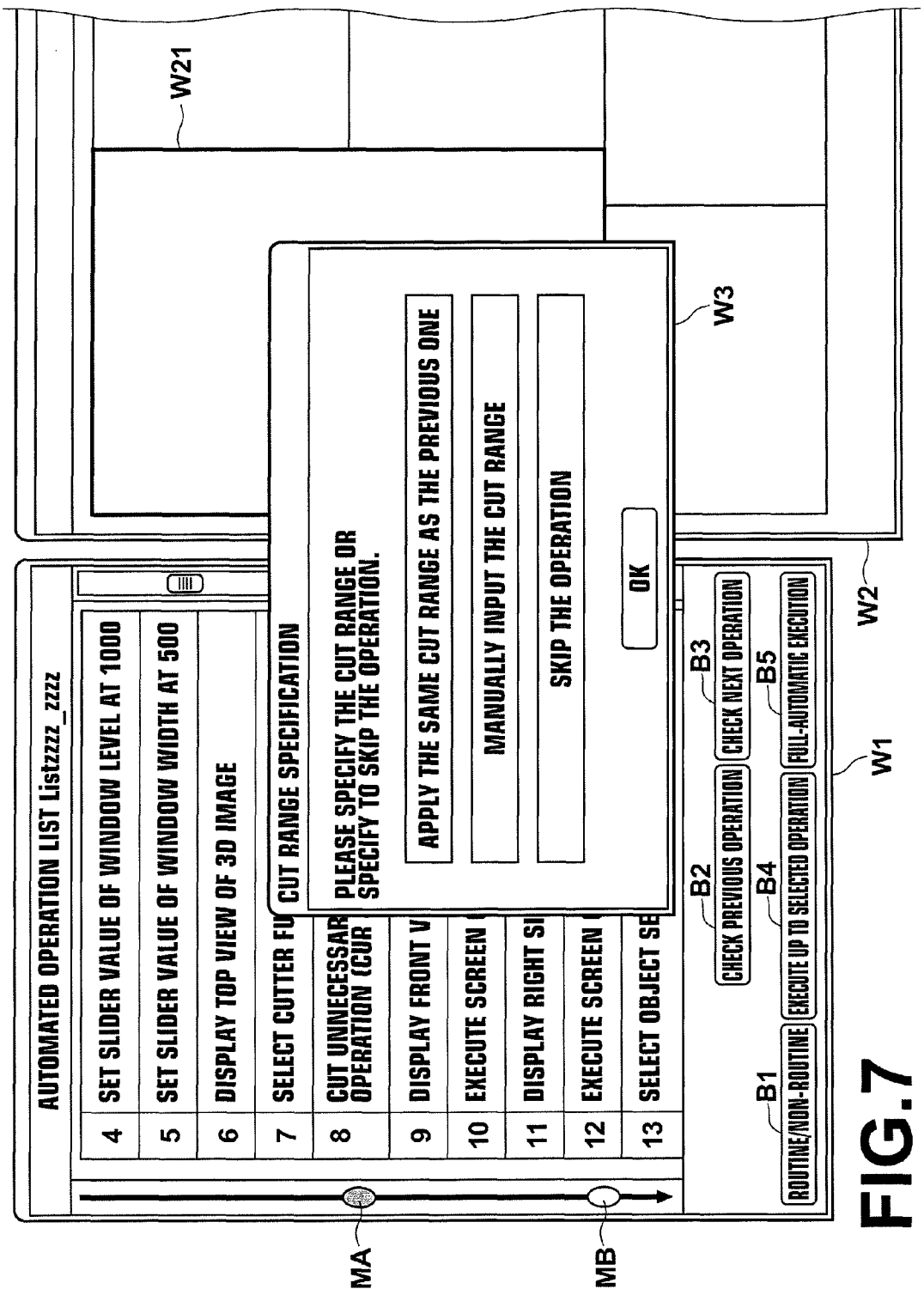
FIG. 7 is a diagram for explaining how a processing parameter of a non-routine operation in the automated operation list is specified in the automated operation list generation method of the first embodiment.
Figure 8:
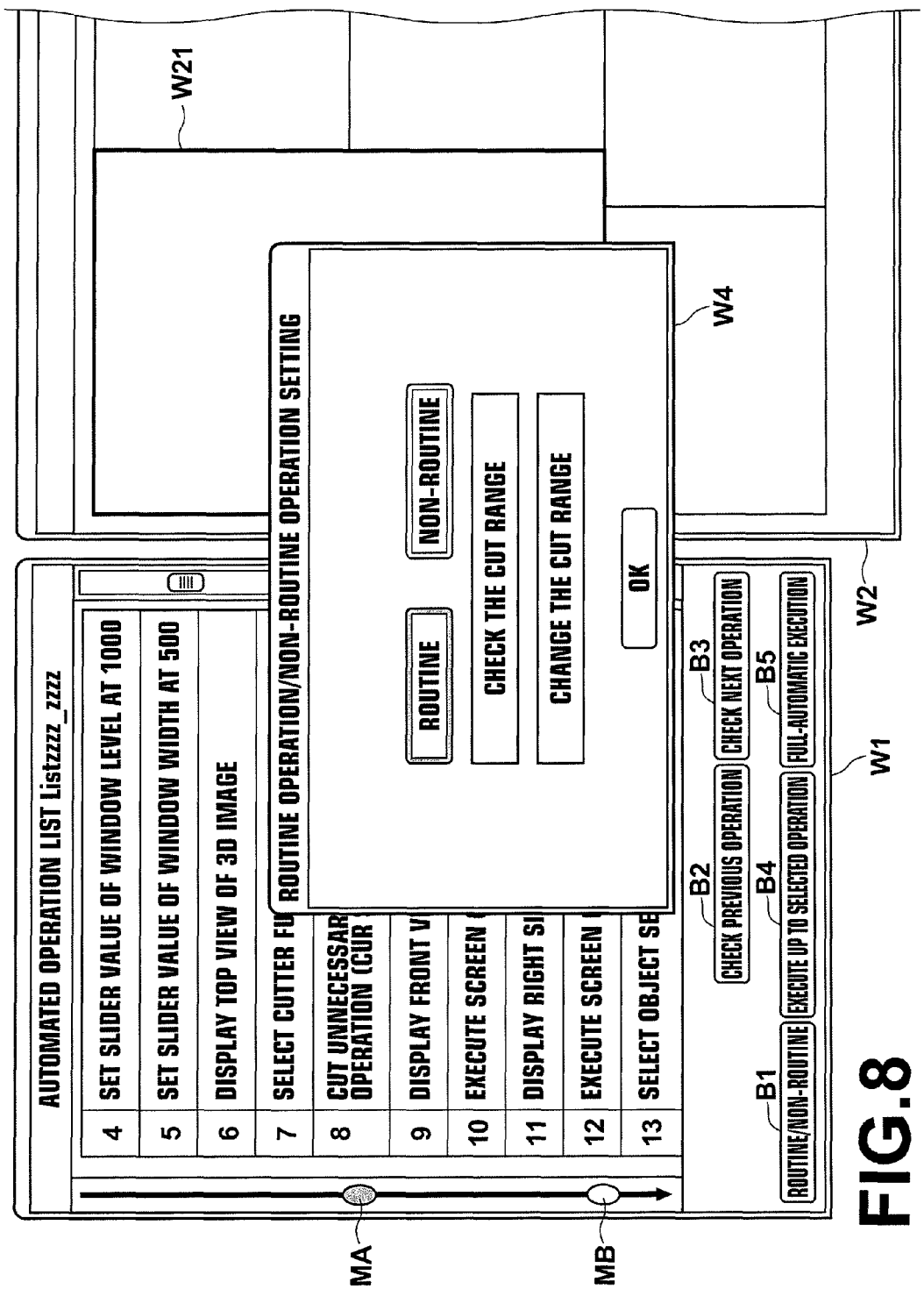
FIG. 8 is a diagram for explaining how a non-routine operation in the automated operation list is changed into a routine operation, and vice versa, in the automated operation list generation method of the first embodiment.

FIG. 6 is a flow chart illustrating the flow of the automated operation list generation method of the first embodiment (the stage of executing the automated operation list). FIG. 7 is a diagram for explaining how a processing parameter of a non-routine operation in the automated operation list is specified in the automated operation list generation method of the first embodiment. FIG. 8 is a diagram for explaining how a non-routine operation in the automated operation list is changed into a routine operation, and vice versa, in the automated operation list generation method of the first embodiment.

Now, how the generated automated operation list is executed is described with reference to FIGS. 6 to 8. First, the user selects an automated operation list execution function in a state where the cerebral artery analysis application is activated, and specifies the automated operation list L to be executed. Then, the specified automated operation list L is loaded from the storage 2 into the memory (S21).

Further, in this embodiment, the display controlling means 15 causes the image of result of each operation, as shown in FIG. 4, to be displayed on the display device 3 synchronously with execution of each operation in the automated operation list L, and causes the automated operation list L to be displayed on the display device 3 such that the operation being executed is identifiable synchronously with execution of each operation in the automated operation list L. In the example shown in FIG. 4, the analysis application window W2, which is the work space for the activated analysis application, containing the display window W21 for displaying the image of interest is displayed. Further, the automated operation list display window W1 containing the automated operation list L is displayed. The analysis application window W2 contains a plurality of windows including the image display window W21 for displaying the image of interest.

In the example shown in FIG. 4, the fourth to thirteenth operations in the automated operation list L (a consecutive part of the operations) are displayed in the automated operation list display window W1. The display range of the automated operation list L can be changed via a scrollbar displayed on the right of the automated operation list display window W1. A marker MA is displayed at the side of the operation which is currently executed so that the user can identify the operation which is currently automatically executed. A marker MB is displayed at the side of each non-routine operation so that the user can identify the non-routine operations that require input of a processing parameter by the user.

The display screen further contains: a routine/non-routine switching button B1 for changing a non-routine operation into a routine operation, and vice versa, to change the automated operation list; a "check previous operation" button B2 for cancelling a result of a routine operation (s) executed after a non-routine operation that is nearest in the order of execution to the currently executed operation (hereinafter, the last-executed non-routine operation) among the non-routine operations before the currently executed operation, and specifying to execute the automated operation list from the last-executed non-routine operation; a "check next operation" button B3 for specifying to automatically execute a routine operation (s) between the currently executed operation and a non-routine operation that is nearest in the order of execution to the currently executed operation (hereinafter, the next non-routine operation) among the non-routine operations after the currently executed operation in the automated operation list L; an "execute up to selected operation" button B4 for automatically executing the automated operation list L from the first operation to an operation selected via the input device 4, such as the mouse, before the button B4 is selected; and an "full-automatic execution" button B5 for specifying to automatically execute the automated operation list L from the start to the end with skipping the non-routine operations. The user can select one of these execution buttons B2 to B4 with the mouse, or the like, to execute the automated operation list L according to the manner of execution set for each button.

After the automated operation list is obtained, the executing means 13 obtains the earliest operation in the order among the operations in the automated operation list L which have not been executed (S22). If the obtained operation is a routine operation (YES at S23), the obtained operation is automatically executed with using the associated processing parameter registered in the automated operation list L (S25).

The executing means 13 in this embodiment automatically executes the generated automated operation list L by receiving input by the user as to whether to execute or skip each non-routine operation registered in the automated operation list L during execution of the automated operation list L. If the obtained operation is the non-routine operation (NO at S23), the executing means 13 prompt the user to make necessary input for executing the non-routine operation, and detects the input by the user to obtain the instruction by the user (S24). Then, the executing means 13 executes or skips the non-routine operation according to the obtained instruction (S25).

In this example, when the executing means 13 executes each non-routine operation in the automated operation list L, a processing parameter setting window W3 is displayed, as shown in FIG. 7, to prompt the user to select whether i) to automatically execute the obtained operation with using the associated processing parameter registered in the automated operation list L, ii) to manually input a necessary processing parameter for the non-routine operation, or iii) to skip the non-routine operation.

If i) is selected, the executing means 13 automatically executes the obtained operation with using the associated processing parameter registered in the automated operation list L. If ii) is selected, the executing means 13 detects manual input by the user to obtain a necessary processing parameter for the non-routine operation and executes the non-routine operation with using the obtained processing parameter. If iii) is selected, the executing means 13 skips the non-routine operation. It should be noted that, in the example shown in FIG. 7, any one of i) an "apply the same cut range as the previous one" button, ii) a "manually input the cut range" button and iii) a "skip the operation" button can be specified by selecting the corresponding one of the buttons of i), ii) and iii) and then pressing the OK button. If it is selected to manually input the cut range, a processing parameter for specifying the cut range is obtained by receiving and detecting manual input of the cut range made by the user with the mouse on the image displayed in the image display window W21 in the analysis application window W2. Then, the eighth operation in the automated operation list L, shown in FIG. 4, is executed.

It should be noted that it is not necessary to always receive an instruction by the user for each non-routine operation in the automated operation list L. For example, the user may set in advance in the automated operation list L to skip the non-routine operations so that the executing means automatically executes the operations forming the process to generate an image according to a desired purpose in the automated operation list L without a pause.

The executing means 13 repeats the operations in S22 to S25 before the operations in S22 to S25 are conducted for all the operations in the automated operation list L (NO at S26). Then, when the operations in S22 to S25 have been conducted for all the operations in the automated operation list L (YES at S26), the execution of the automated operation list L ends.

Now, how a non-routine operation in the generated automated operation list L is changed into a routine operation, and vice versa, by the changing means 14 according to this embodiment is described. When the user selects the routine operation/non-routine operation switching button B1 in the automated operation list display window W1 in the state where the automated operation list display window W1 and the analysis application window W2 are displayed, as shown in FIG. 4, a routine operation/non-routine operation setting window W4 is further displayed, as shown in FIG. 8.

FIG. 8 schematically shows a state where the automated operation list L shown in FIG. 4 is executed in the order of registration and the routine operation/non-routine operation switching button B1 is selected by the user when the eighth operation in the automated operation list L, namely, the operation to cut the skin surface of the face, which is a non-routine operation, is executed. The user can check the associated processing parameter in the automated operation list L by selecting a "check the cut range" button. In this example, a processing parameter for specifying the cut range that was used the last time the operation to cut the skin surface of the face was executed is registered as the associated processing parameter in the automated operation list L. If this operation to cut the skin surface of the face, which is registered in the automated operation list L as the non-routine operation, is changeable into a routine operation with using the processing parameter checked by the user, the user selects a "routine" button and then clicks on the OK button.

Then, the changing means 14 receives this click on the OK button, changes the classification of the operation to cut the skin surface of the face from the non-routine operation to the routine operation to update the content of the automated operation list L, and stores the updated automated operation list L in the storage 2.

If the user wishes to specify a new cut range as the processing parameter for the non-routine operation, rather than using the associated processing parameter in the automated operation list L, the user can select a "change the cut range" button and specify the new cut range on the display image with the mouse, or the like, to associate the new cut range with the operation in the automated operation list L. Further, if the operation to cut the skin surface of the face is changeable into a routine operation with using the new cut range as the processing parameter, the user selects the "routine" button and then clicks on the OK button. Then, as described above, the changing means 14 receives this click on the OK button, changes the classification of the operation to cut the skin surface of the face from the non-routine operation to the routine operation to update the content of the automated operation list L, and stores the updated automated operation list L in the storage 2.

Further, the changing means 14 according to this embodiment can change a routine operation in the generated automated operation list L into a non-routine operation based on further input received by the inputting means 4. In the case where a routine operation in the automated operation list L is changed into a non-routine operation, the user selects a certain routine operation registered in the automated operation list L, and then selects the routine operation/non-routine operation switching button B1 shown in FIG. 4. Then, the routine operation/non-routine operation setting window W4 is displayed, as shown in FIG. 8. When the user selects a "non-routine" button and clicks on the OK button, the changing means 14 receives this click on the OK button, changes the classification of the selected operation from the routine operation to the non-routine operation to update the content of the automated operation list L, and stores the updated automated operation list L in the storage 2.

It should be noted that, although it is preferred that the changing operation by the changing means 14 is conducted synchronously with the progress of the automated operation list L, which is executed in the order of registration of the operations, this is not intended to limit the present invention. For example, a GUI, as shown in FIG. 8, may be used to display the automated operation list L without executing the automated operation list L, and the user may select a desired operation from the automated operation list L via the input device 4. Then, the user may select the routine operation/non-routine operation switching button B1 and specify a necessary processing parameter when the desired operation is a non-routine operation and is to be changed into a routine operation. Further alternatively, the user may directly change the data file of the automated operation list L.

As described above, according to this embodiment, the inputting means 4 receives selection of operations in a desired order by the user and receives, as necessary, input of processing parameters, the operation information obtaining means 11 obtains, based on each operation corresponding to the input received by the inputting means 4, the operation information, which classifies each operation corresponding to the input into the non-routine operation, which requires input of a processing parameter during execution of the automated operation list, or the routine operation other than the non-routine operation in advance, and the automated operation list generating means 12 generates the automated operation list based on the obtained operation information by registering, if the operation corresponding to the input is a routine operation, the operation corresponding to the input with associating, as necessary, a necessary processing parameter for the operation therewith in the automated operation list, and registering, if the operation corresponding to the input is a non-routine operation, the operation corresponding to the input in the automated operation list. Thus, the user only needs to execute a plurality of operations, which form a process to generate an image according to a desired purpose, in a desired order to generate the automated operation list, in which each operation forming the process to generate an image according to a desired purpose is classified into the routine operation or the non-routine operation and the necessary processing parameter for each routine operation is associated with the routine operation, as necessary. This reduces the burden of troublesome operations of determining whether or not each operation forming the process to generate an image according to a desired purpose is a routine operation and specifying, as necessary, a necessary processing parameter for each routine operation during generation of the automated operation list.

Further, according to this embodiment, the changing means 14 for changing a non-routine operation in the generated automated operation list L into a routine operation based on further input received by the inputting means 4 is further provided. Thus, changing of the classification of each operation (i.e., whether it is a routine operation or a non-routine operation) in the automated operation list L generated according to a desired purpose can be achieved easily and flexibly, thereby facilitating generation of the automated operation list as required by the user.

Yet further, the changing means 14 according to this embodiment can change a routine operation in the generated automated operation list L into a non-routine operation based on further input received by the inputting means 4. In this case, changing of the classification of each operation (i.e., whether it is a routine operation or a non-routine operation) in the automated operation list generated according to a desired purpose can be achieved easily and flexibly, thereby facilitating generation of the automated operation list as required by the user.

Still further, according to this embodiment, the executing means 13 for automatically executing each operation registered in the automated operation list L in the order of registration of the operations in the automated operation list L is provided, where if the operation to be executed is a routine operation, the routine operation is automatically executed with using an associated processing parameter registered in the automated operation list, and if the operation to be executed is a non-routine operation, input by the user as to whether to execute or skip the non-routine operation is received, and then, if it is selected to execute the non-routine operation, the non-routine operation is executed. Therefore, the user only needs to input selection as to whether to execute or skip each non-routine operation during execution of the automated operation list L, and thus can easily execute the plurality of operations for generating a desired image based on the generated automated operation list L.

Further, the automated operation list generating means 12 also registers, if the operation corresponding to the input is a non-routine operation, the operation corresponding to the input in the automated operation list with associating a necessary processing parameter for the operation with the operation, and the executing means 13 receives, if the operation to be executed is a non-routine operation, input of selection by the user as to whether to obtain the associated processing parameter registered in the automated operation list or to receive input of a processing parameter by the user, and causes the non-routine operation to be executed with suing the selected processing parameter. Therefore, if the processing parameter registered in the automated operation list is used, input of the processing parameter for the non-routine operation by the user during execution of the automated operation list can be omitted based on the generated automated operation list, thereby facilitating execution of the plurality of operations for generating a desired image.

Further, at least one of the automated operation list generating means 12 and the changing means 14 according to this embodiment can set, in the automated operation list L, whether or not to skip each non-routine operation registered in the automated operation list L during execution of the automated operation list, and the executing means does not execute the non-routine operation which is set to be skipped during execution of the automated operation list. Therefore, the automated operation list generating means 12 or the changing means 14 registers, for each non-routine operation registered in the automated operation list L, the skip information as to whether or not to skip the non-routine operation. In this case, input by the user as to whether to execute or skip each non-routine operation during execution of the automated operation list L can be omitted for the non-routine operation which is set to be skipped, and thus the plurality of operations for generating a desired image can be executed easily based on the generated automated operation list.

According to this embodiment, the display controlling means 15 for displaying the automated operation list on the display device such that the operation being executed is identifiable synchronously with execution of each operation in the automated operation list is provided. Therefore, understanding of the operations for generating a desired image registered in the automated operation list and the order of automatic execution of the operations is facilitated.

According to this embodiment, the display controlling means 15 displays the image of result of each operation on the display device synchronously with execution of each operation in the automated operation list. Therefore, understanding of the operations for generating a desired image registered in the automated operation list is facilitated. In this embodiment, both the automated operation list and the image of result of each operation are displayed synchronously with the progress of the automated operation list, and thus the above-mentioned advantage is enhanced.

Further, in this embodiment, even an operation that requires a different processing parameter each time the automated operation list L is executed may be registered as a routine operation in the automated operation list L by associating information that can indirectly specify the processing parameter with the operation, such as by registering, as the processing parameter for the "operation to select a 3D image", information specifying the type of display window which displays the 3D image of interest in the automated operation list L. This can minimize the number of non-routine operations in the automated operation list L, thereby significantly reducing input operations by the user.

The automated operation list generation device may further include a means for causing, with using any known method, the executing means 13 to execute the automated operation list L in response to activation of an image analysis application, and the executing means 13 may execute the automated operation list L in response to activation of the image analysis application. Further, the automated operation list generation device may further include a means for specifying, for example, a medical image registered at a predetermined address of a storage as a medical image of interest, and causing, with using any known method, the executing means 13 to execute the automated operation list L in response to selection of the medical image, and the executing means 13 may execute the automated operation list L in response to selection of the medical image of interest. In this case, input by the user to activate the execution of the automated operation list can be omitted, thereby facilitating execution of the automated operation list.

In this embodiment, the executing means 13 can execute the automated operation list in various manners, such as automatic execution or stepwise execution of the operations in an arbitrary range of the automated operation list L. This allows flexible execution of the automated operation list as required by the user, thereby facilitating utilization of the automated operation list.

Further, in this embodiment, the changing means 14 is able to change a non-routine operation in the automated operation list into a routine operation, and vice versa, during execution of the automated operation list. Therefore, the user can check the result of the operation that has just been executed in the automated operation list L synchronously with the progress of execution of the automated operation list L by the executing means 13, and can determine whether or not the classification of the operation which has been executed just before the automated operation list L is temporarily stopped should be changed into the routine operation depending on the checked result of the operation. In this case, the user can determine whether or not a certain operation should be handled as a routine operation based on the result of automatic execution, and this facilitates accurate determination of the classification of each operation (i.e., whether it is a routine operation or a non-routine operation).

Now, a second embodiment of the invention is described.

Figure 9:
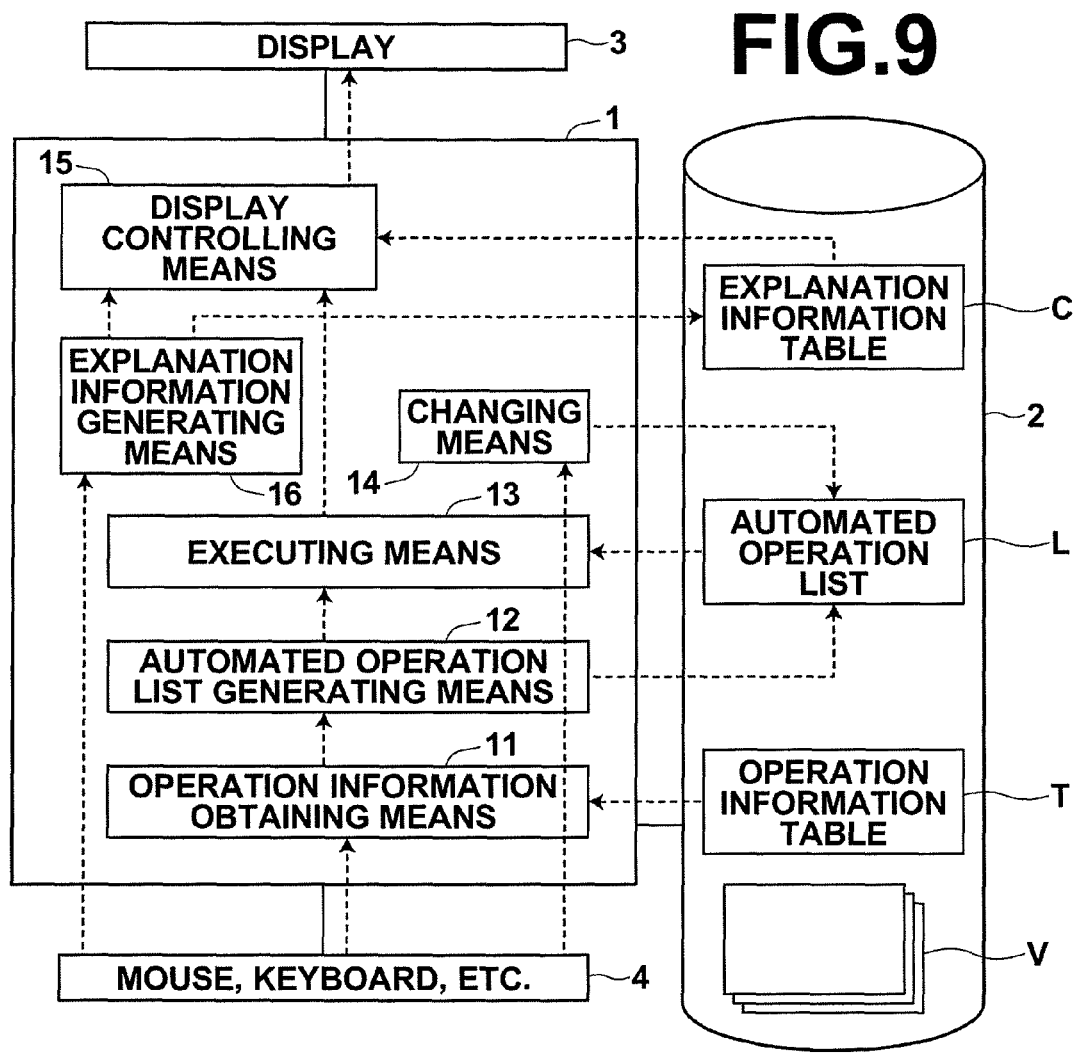
FIG. 9 is a diagram illustrating the schematic configuration of an automated operation list generation device of a second embodiment.

FIG. 9 is a diagram illustrating the schematic configuration of an automated operation list generation device according to a second embodiment. The difference between the automated operation list generation device of the second embodiment and the device of the first embodiment lies in that the device of the second embodiment further includes an explanation information generating means 16.

The following description of the second embodiment is focused on different points from the first embodiment, and descriptions of the same elements as those of the first embodiment are omitted.

The explanation information generating means 16 generates, for each operation in the automated operation list L, explanation information, such as a picture, words or a text, which explains the operation. In this embodiment, the user executes the generated automated operation list in a stepwise manner, and temporarily stops the execution of the automated operation list L at each operation that requires an explanation to be added. Then, the user selects, via the input device 4, or the like, the operation, for which the explanation information is to be generated or edited, in the automated operation list L displayed in the automated operation list display window W1 and inputs or changes the explanation information of the selected operation. The explanation information generating means 16 obtains the selection of the operation for which the explanation information is generated or edited and the input of the explanation information to generate an explanation information table C, which associates the obtained explanation information with each selected operation, and stores the explanation information table C in the storage 2. Alternatively, the explanation information generating means 16 may generate the automated operation list L which includes the explanation information table C by associating each operation in the automated operation list L with the corresponding explanation information, or may generate the explanation information in any form. It should be noted that it is not necessary for the user to generate the explanation information for every operation registered in the automated operation list L. The user may generate the explanation information for only the operations, for which the user determines that it is necessary to add explanation.

Figure 10:
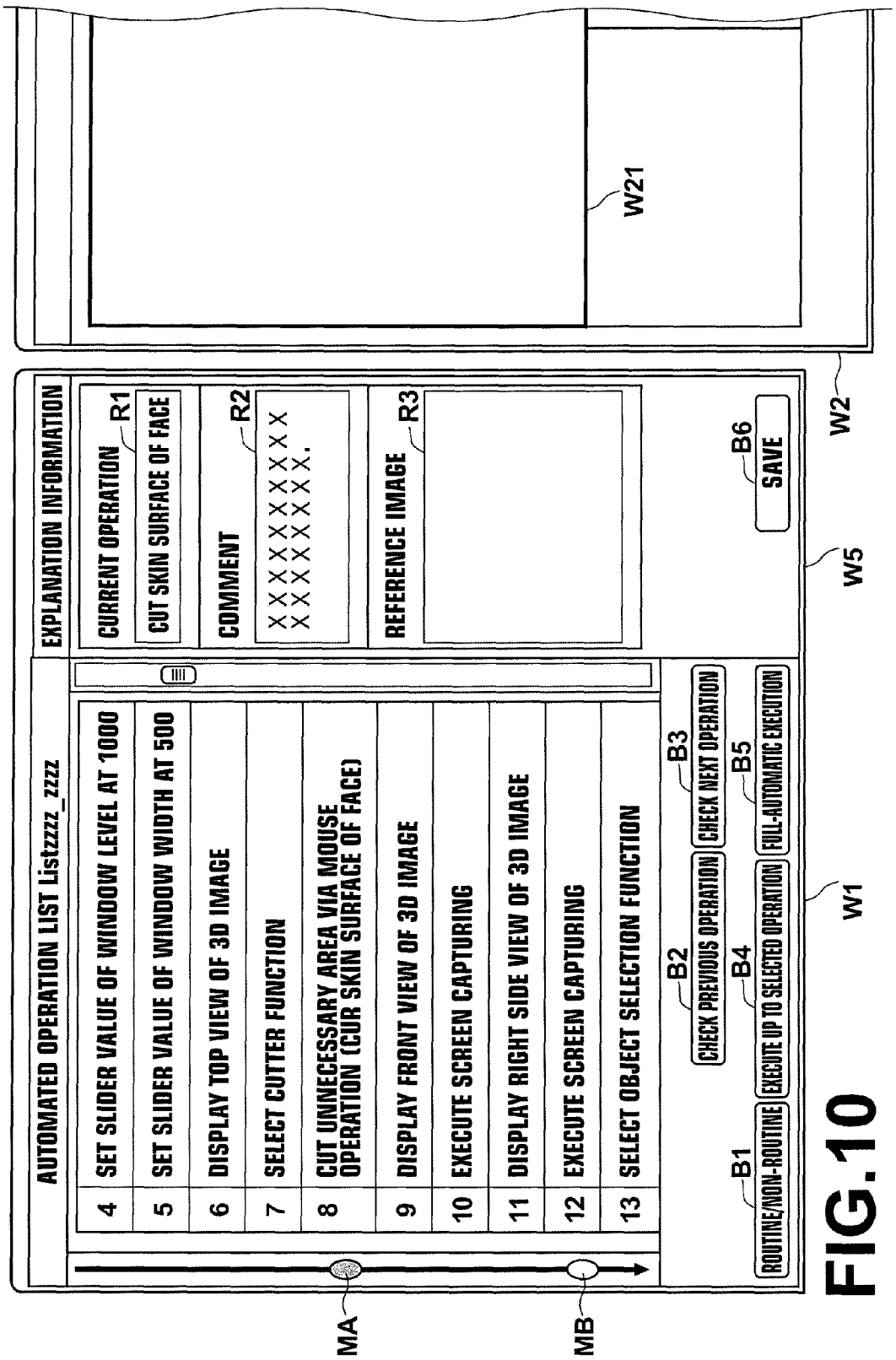
FIG. 10 is a diagram for explaining how explanation information is generated with the automated operation list generation device of the second embodiment.

FIG. 10 is a diagram for explaining a display screen for displaying the explanation information of the automated operation list generation device of the second embodiment. The user can generate, update and display the explanation information on the display screen as shown in FIG. 10. In this embodiment, the user executes the generated automated operation list L in a stepwise manner, and inputs, for each operation, the explanation information that explains the operation in areas R1, R2 and/or R3 of an explanation information display window W5 via the input device 4. Then, the explanation information generating means 16 detects this input, and registers the explanation information for each operation in the explanation information table C. The explanation information generating means 16 detects the content of the explanation information inputted by the user when the user clicks on a save button B6 and at predetermined time intervals, and updates the registration or change of the explanation information in the explanation information table C.

Any of various types of information can be registered as the explanation information as required by the user. For example, in the outline description area R1 of the explanation information window W5, words or a text describing the outline of the currently executed operation is inputted or displayed as the explanation information, as shown in FIG. 10. In the comment area R2, comments, such as precautions when the user executes the operation and/or detailed description of the operation, made by the user are inputted or displayed as the explanation information. In the reference image area R3, a reference image describing the operation, such as an image of result of the operation, is inputted or displayed as the explanation information.

Generation and update of the explanation information may be achieved with any of various known methods. By generating, updating, or displaying the explanation information synchronously with execution of the automated operation list L, as in this embodiment, the user can understand each operation forming the process to generate an image according to a desired purpose in the automated operation list L and the explanation information relating to each operation in an associated manner, thereby facilitating generation and update of the explanation information by the user and display of the explanation information in an efficient manner.

According to the second embodiment, the explanation information generating means 16 for storing the explanation information, which explains each operation in the automated operation list, in an editable manner is further provided, and the display controlling means 15 displays the explanation information on the display device 3 synchronously with execution of each operation in the automated operation list. Therefore, even a third person who is not familiar with the operations for generating a desired image can execute the automated operation list with referring to the explanation information, such as the order, the purpose and/or precautions of the operations forming the automated operation list. This helps the user to understand the operations for generating a desired image registered in the automated operation list and to use the automated operation list.

In particular, generating and displaying the explanation information for the non-routine operations that require input of processing parameters by the user helps execution of the operations forming the process according to a desired purpose by a third person who is not familiar with the operations. Further, the explanation information can be used as an aid of explanation when the user who well understands the operations forming the process according to a desired purpose directly explains the operations to a third person. Alternatively, explanation of the operations forming the process according to a desired purpose can indirectly be achieved by prompting a third person to reference the data of the automated operation list and the explanation information. In this manner, the explanation information of the operations forming the process according to the purpose can be used easily.

In particular, in the case of image processing conducted at a medical institution, where the process to generate an image according to a desired purpose varies in details at each hospital or each diagnosis and treatment department and it requires much specific knowledge, such as the purpose and precautions of each operation, to execute each operation forming each process to generate an image according to a desired purpose, the explanation information contributes largely to reducing a burden imposed on the user when the user, who has enough knowledge about the process to generate an image according to each purpose, explains the process to generate an image according to the purpose to a third person.

It should be noted that an explanation information DB which associates each operation with the corresponding explanation information generated in advance by the user may be prepared in advance, and the explanation information generating means 16 may obtain the explanation information corresponding to each operation in the automated operation list L from the explanation information DB and associate each operation in the automated operation list L with the corresponding explanation information to generate the explanation information table C. Alternatively, the explanation information table C may be generated or edited on any of various known GUIs, as described above, or the data file of the explanation information table C may directly be generated or edited. Further alternatively, the explanation information table C may be generated in the stage of generating the automated operation list in such a manner that the operations forming the process according to a desired purpose are executed in order and the user inputs the explanation information during generation of the automated operation list.

It should be noted that the above-described embodiments are not intended to limit the present invention. Various changes may be made to the invention without departing from the scope and spirit of the invention.

Further, it is apparent to those skilled in the art that the automated operation list generation method according to the embodiment of the invention is applicable not only to generation of an automated operation list relating to processing of a medical image but also to generation of various automated operation lists for processing an image virtually generated with a CG technique, an image taken with a digital camera, etc.

Still further, the automated operation list generation device of the invention may be implemented with a plurality of computers, where the functions as the input device 4, the operation information obtaining means 11, the automated operation list generating means 12, the executing means 13, the changing means 14, the display controlling means 15 and the explanation information generating means 16 are divided among these computers. As the devices forming the system, such as the input device, the display, etc., any known devices may be used. For example, a joystick may be used in place of the mouse, and a touch panel may be used in place of the display.

What is claimed is:

1. An automated operation list generation device for generating an automated operation list, the automated operation list causing a plurality of operations, which form a process to generate an image according to a desired purpose, to be automatically executed in a desired order with using an image analysis application that is able to execute the operations in any order according to input by the user, the device comprising:

a processing device including a central processing unit (CPU); and
an inputting unit configured to receive an input of selection of a desired operation from the operations in a desired order and, as necessary, input of a necessary processing parameter for the selected operation,
wherein said CPU is configured to perform as:
an operation information obtaining unit configured to obtain operation information based on the operation corresponding to the input received by the inputter, the operation information classifying the operation corresponding to the input into a non-routine operation, which requires input of a processing parameter during execution of the automated operation list, or a routine operation other than the non-routine operation in advance; and an automated operation list generating unit configured to generate the automated operation list based on the obtained operation information by registering, if the operation corresponding to the input is a routine operation, the operation corresponding to the input in the automated operation list with associating, as necessary, a necessary processing parameter for the operation with the operation, and if the operation corresponding to the input is a non-routine operation, registering the operation corresponding to the input in the automated operation list.

2. The automated operation list generation device as claimed in claim 1, further comprising a changing unit for changing a non-routine operation in the generated automated operation list into a routine operation based on further input received by the inputting unit.

3. The automated operation list generation device as claimed in claim 2, wherein the changing unit is able to change a routine operation in the generated automated operation list into a non-routine operation based on further input received by the inputting unit.

4. The automated operation list generation device as claimed in claim 1, further comprising an executing unit for causing the operations registered in the automated operation list to be automatically executed in an order of registration of the operations in the automated operation list, wherein, if an operation to be executed is a routine operation, the routine operation is automatically executed with using a processing parameter associated with the routine operation registered in the automated operation list, and if an operation to be executed is a non-routine operation, input of selection by the user as to whether to execute or skip the non-routine operation is received, and then if it is selected to execute the non-routine operation, the non-routine operation is executed.

5. The automated operation list generation device as claimed in claim 4, wherein
the automated operation list generating unit also registers, if the operation corresponding to the input is a non-routine operation, the operation in the automated operation list with associating a necessary processing parameter for the operation with the operation, and
the executing unit receives, if the operation to be executed is a non-routine operation, input of selection by the user as to whether to obtain the processing parameter registered in the automated operation list or to receive input of the processing parameter by the user, and causes the non-routine operation to be executed with using the selected processing parameter.

6. The automated operation list generation device as claimed in claim 4, wherein
at least one of the automated operation list generating unit and the changing unit is able to set in the automated operation list whether or not to skip each non-routine operation registered in the automated operation list during execution of the automated operation list, and
the executing unit does not execute the non-routine operation which is set to be skipped during execution of the automated operation list.

7. The automated operation list generation device as claimed in claim 1, further comprising a display controlling unit for displaying the automated operation list on a display device such that the operation being executed is identifiable synchronously with execution of each operation in the automated operation list.

8. The automated operation list generation device as claimed in claim 7, wherein the display controlling unit displays an image of result of each operation on the display device synchronously with execution of each operation in the automated operation list.

9. The automated operation list generation device as claimed in claim 7, further comprising an explanation information generating unit for storing explanation information in an editable manner, the explanation information explaining each operation in the automated operation list,
wherein the display controlling unit displays the explanation information on the display device synchronously with execution of each operation in the automated operation list.

10. The automated operation list generation device as claimed in claim 4, wherein the executing unit executes the automated operation list in response to activation of the image analysis application.

11. The automated operation list generation device as claimed in claim 4, wherein the executing unit executes the automated operation list in response to selection of a medical image of interest.

12. An automated operation list generation method implemented by a computer for generating an automated operation list, the automated operation list causing a plurality of operations, which form a process to generate an image according to a desired purpose, to be automatically executed in a desired order with using an image analysis application that is able to execute the operations in any order according to input by the user, the method comprising:
receiving input of selection of a desired operation from the operations in a desired order and, as necessary, input of a processing parameter;
obtaining operation information based on the operation corresponding to the received input, the operation information classifying the operation corresponding to the input into a non-routine operation, which requires input of a processing parameter during execution of the automated operation list, or a routine operation other than the non-routine operation in advance; and
generating the automated operation list based on the obtained operation information by registering, if the operation corresponding to the input is a routine operation, the operation corresponding to the input in the automated operation list with associating, as necessary, a necessary processing parameter for the operation with the operation, and registering, if the operation corresponding to the input is a non-routine operation, the operation corresponding to the input in the automated operation list.

13. A non-transitory computer-readable storage medium containing an automated operation list generation program which generates an automated operation list, the automated operation list causing a plurality of operations, which form a process to generate an image according to a desired purpose, to be automatically executed in a desired order with using an image analysis application that is able to execute the operations in any order according to input by the user, the program causing a computer to function as:
an inputting unit configured to receive an input of selection of a desired operation from the operations in a desired order and, as necessary, an input of a necessary processing parameter for the selected operation;
an operation information obtaining unit configured to obtain operation information based on the operation corresponding to the input received by the inputting unit, the operation information classifying the operation corresponding to the input into a non-routine operation, which requires input of a processing parameter during execution of the automated operation list, or a routine operation other than the non-routine operation in advance; and an automated operation list generating unit configured to generate the automated operation list based on the obtained operation information by registering, if the operation corresponding to the input is a routine operation, the operation corresponding to the input in the automated operation list with associating, as necessary, a necessary processing parameter for the operation with the operation, and if the operation corresponding to the input is a non-routine operation, registering the operation corresponding to the input in the automated operation list.

\* \* \* \* \*